US009944803B2

(12) United States Patent
Matson et al.

(10) Patent No.: US 9,944,803 B2
(45) Date of Patent: Apr. 17, 2018

(54) METHODS OF MERCAPTANIZING UNSATURATED COMPOUNDS AND COMPOSITIONS PRODUCED THEREFROM

(71) Applicant: Chevron Phillips Chemical Company LP, The Woodlands, TX (US)

(72) Inventors: Michael S. Matson, Bartlesville, OK (US); Colin Cameron, Stocksfield (GB); Anthony Colin Wright, Newcastle Upon Tyne (GB); Ian David Fletcher, Newcastle Upon Tyne (GB)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 157 days.

(21) Appl. No.: 14/886,146

(22) Filed: Oct. 19, 2015

(65) Prior Publication Data
US 2016/0040051 A1 Feb. 11, 2016

Related U.S. Application Data

(63) Continuation of application No. 13/677,405, filed on Nov. 15, 2012, now abandoned.

(51) Int. Cl.
| | |
|---|---|
| C09J 181/04 | (2006.01) |
| C09D 181/04 | (2006.01) |
| C09D 7/12 | (2006.01) |
| C07D 251/34 | (2006.01) |
| C08K 5/378 | (2006.01) |
| C07C 323/12 | (2006.01) |
| C08G 59/66 | (2006.01) |

(52) U.S. Cl.
CPC .......... *C09D 7/1233* (2013.01); *C07C 323/12* (2013.01); *C07D 251/34* (2013.01); *C08G 59/66* (2013.01); *C08K 5/378* (2013.01); *C09D 181/04* (2013.01); *C09J 181/04* (2013.01)

(58) Field of Classification Search
CPC .................................................. C07C 323/12
See application file for complete search history.

(56) References Cited

U.S. PATENT DOCUMENTS

| | | | |
|---|---|---|---|
| 2,445,142 A | 7/1948 | Himel | |
| 2,458,075 A | 1/1949 | Himel | |
| 2,587,580 A | 3/1952 | McCool | |
| 2,626,279 A | 1/1953 | Crouch et al. | |
| 2,639,293 A | 5/1953 | Crouch | |
| 3,081,352 A | 3/1963 | Gardner et al. | |
| 3,223,738 A | 12/1965 | Crain et al. | |
| 3,397,243 A | 8/1968 | Kite | |
| 3,505,166 A | 4/1970 | Jones et al. | |
| 3,616,374 A | 10/1971 | Goshorn et al. | |
| 3,624,160 A | 11/1971 | Jones et al. | |
| 3,625,925 A | 12/1971 | Oswald et al. | |
| 3,632,654 A | 1/1972 | Van Auken et al. | |
| 3,823,191 A | 7/1974 | Dighe | |
| 3,883,598 A | 5/1975 | Guthrie et al. | |
| 3,940,374 A | 2/1976 | Oswald et al. | |
| 3,954,800 A | 5/1976 | Lowe | |
| 3,981,901 A | 9/1976 | Guthrie et al. | |
| 3,981,904 A | 9/1976 | Guthrie et al. | |
| 3,984,456 A | 10/1976 | Guthrie et al. | |
| 3,998,866 A | 12/1976 | Oswald | |
| 4,045,317 A | 8/1977 | Larsen | |
| 4,045,472 A | 8/1977 | Guthrie et al. | |
| 4,059,610 A | 11/1977 | Handa et al. | |
| 4,061,864 A | 12/1977 | Guthrie et al. | |
| 4,140,604 A | 2/1979 | Dimmig | |
| 4,266,055 A | 5/1981 | Inoue et al. | |
| 4,612,398 A | 9/1986 | Lee | |
| 5,374,668 A | 12/1994 | Kanemura et al. | |
| 8,461,293 B2 | 6/2013 | Matson et al. | |
| 9,133,370 B2 | 9/2015 | Matson et al. | |
| 9,340,715 B2 | 5/2016 | Matson et al. | |
| 9,340,716 B2 | 5/2016 | Matson et al. | |
| 9,340,717 B2 | 5/2016 | Matson et al. | |
| 2010/0010267 A1 | 1/2010 | Deck et al. | |
| 2012/0035291 A1 | 2/2012 | Matson et al. | |
| 2014/0131618 A1 | 5/2014 | Matson | |
| 2016/0040020 A1 | 2/2016 | Matson et al. | |

FOREIGN PATENT DOCUMENTS

| | | |
|---|---|---|
| CA | 1127645 | 7/1982 |
| DE | 2361769 | 6/1975 |
| EP | 0272181 | 6/1988 |
| FR | 1410892 | 9/1964 |
| FR | 1468193 | 2/1966 |
| GB | 1283832 | 8/1972 |
| GB | 2075493 | 11/1981 |
| JP | 56-120671 | 9/1981 |
| JP | 58-013657 | 1/1983 |
| JP | 10-251222 | 9/1998 |

OTHER PUBLICATIONS

Zapp et al, "Radiation-Induced Crosslinking of Chlorobutyl and Polydiene Elastomers. Promotion by Polythiols," Rubber Chemistry and Technology, vol. 48, pp. 860-877.

Senyurt et al., "Thermal and Mechanical Properties of Cross-Linked Photopolymers Based on Multifunctional Thiol-Urethane Ene Monomers," *Macromolecules* 2007, American Chemical Society, vol. 40, p. 3174.

(Continued)

*Primary Examiner* — Peter F Godenschwager
(74) *Attorney, Agent, or Firm* — Merchant & Gould P.C.

(57) ABSTRACT

The present invention discloses polythiol compositions containing polythiol molecules having both thiol groups and intermolecular sulfide groups. Processes for producing such polythiol compositions also are described.

22 Claims, 3 Drawing Sheets

(56) References Cited

OTHER PUBLICATIONS

International Search Report, PCT/US2011/046186, dated Dec. 22, 2011, 3 pages.
International Search Report, PCT/US2013/069593, dated Mar. 17, 2014, 3 pages.

METHODS OF MERCAPTANIZING UNSATURATED COMPOUNDS AND COMPOSITIONS PRODUCED THEREFROM

CROSS-REFERENCE TO RELATED APPLICATION

This application is a continuation application of co-pending U.S. patent application Ser. No. 13/677,405, filed on Nov. 15, 2012, the disclosure of which is incorporated herein by reference in its entirety.

BACKGROUND OF THE INVENTION

The present invention relates generally to polythiol compositions and to methods for producing such polythiol compositions. These polythiol compositions can be used as curing agents in adhesives, coatings, and other applications.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Various polythiol compositions comprising polythiol molecules are disclosed herein. In one embodiment, a polythiol composition is disclosed, and this composition can comprise polythiol molecules having the following chemical structures:

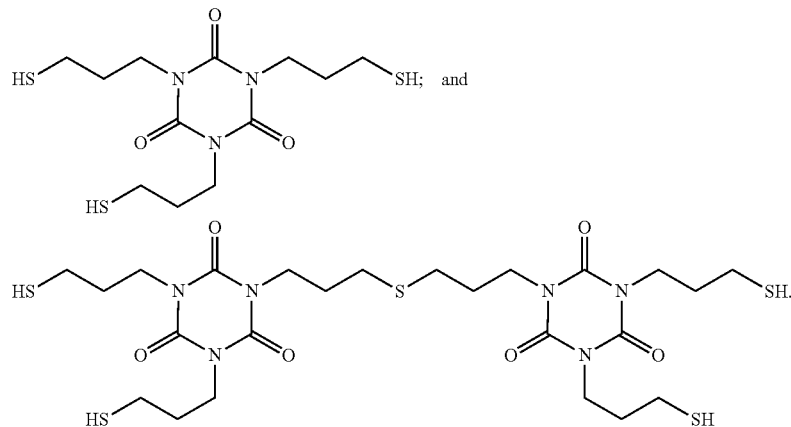

Another polythiol composition comprising polythiol molecules is provided herein, and in this embodiment, the polythiol molecules can have the following chemical structures:

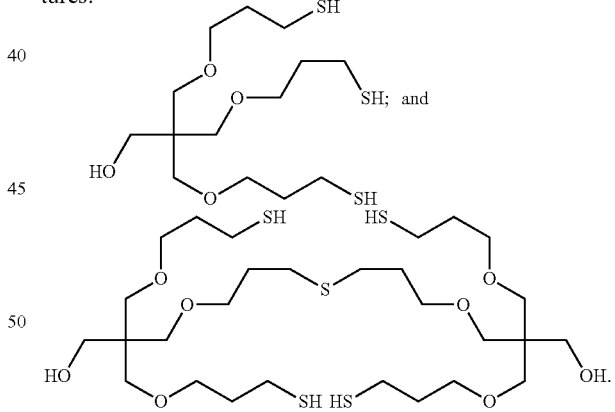

In yet another embodiment, a polythiol composition is described herein which can comprise polythiol molecules having the following chemical formulas, wherein R can be a $C_1$-$C_{18}$ hydrocarbyl group:

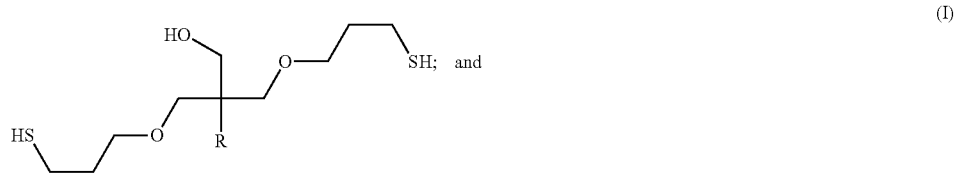

(I)

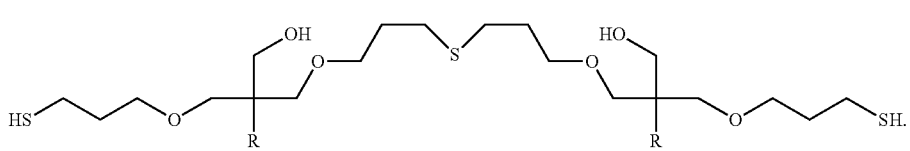

(II)

Processes for forming these polythiol compositions also are disclosed herein. Generally, these processes can comprise contacting $H_2S$, a phosphite compound, and an unsaturated compound having two or three carbon-carbon double bonds; and forming the polythiol composition. The molar ratio of $H_2S$ to carbon-carbon double bonds of the unsaturated compound typically can range from 5:1 to 500:1.

Both the foregoing summary and the following detailed description provide examples and are explanatory only. Accordingly, the foregoing summary and the following detailed description should not be considered to be restrictive. Further, features or variations can be provided in addition to those set forth herein. For example, certain embodiments can be directed to various feature combinations and sub-combinations described in the detailed description.

DEFINITIONS

Figure 1:
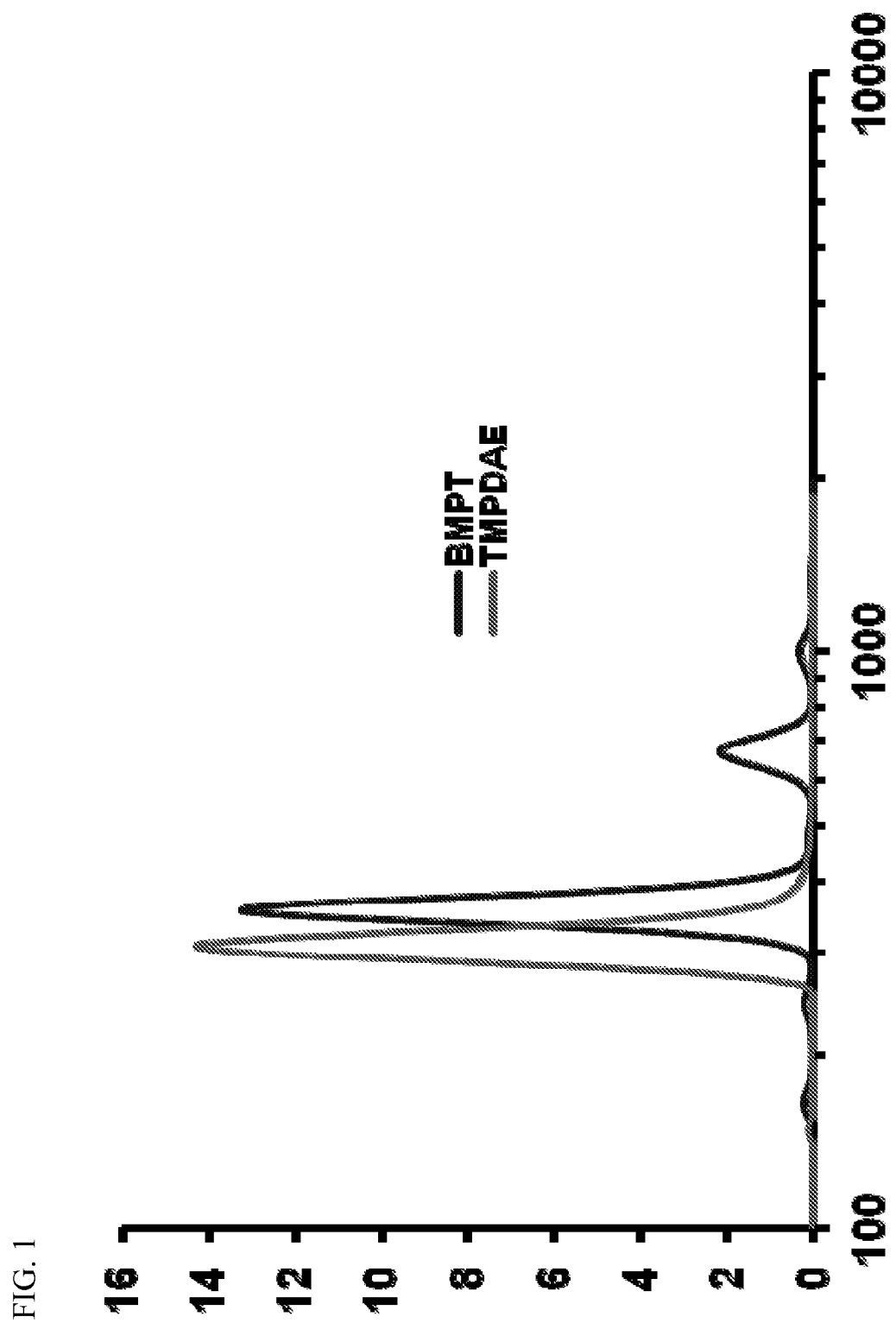
FIG. 1 presents a plot of the molecular weight distributions of TMPDAE and the polythiol composition of Example 9 containing BMPT.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified components or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. For example, a feedstock consisting essentially of component A can include impurities typically present in a commercially produced or commercially available sample of component A. When a claim includes different features and/or feature classes (for example, a method step, feedstock features, and/or product features, among other possibilities), the transitional terms comprising, consisting essentially of, and consisting of, apply only to the feature class to which it is utilized and it is possible to have different transitional terms or phrases utilized with different features within a claim. For example, a method can consist of certain steps, but utilize a reaction mixture comprising recited components and other non-recited components. While compositions and methods are described herein in terms of "comprising" various components or steps, the compositions and methods can also "consist essentially of" or "consist of" the various components or steps, unless stated otherwise. For example, a polythiol composition consistent with embodiments of the present invention can comprise; alternatively, can consist essentially of; or alternatively, can consist of; polythiol molecules having formula (I), and polythiol molecules having formula (II).

The terms "a," "an," and "the" are intended to include plural alternatives, e.g., at least one. For instance, the disclosure of "an unsaturated compound," "a phosphite compound," etc., is meant to encompass one, or mixtures or combinations of more than one, unsaturated compound, phosphite compound, etc., unless otherwise specified.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbyl group" is used herein in accordance with the definition specified by IUPAC: a univalent group formed by removing a hydrogen atom from a hydrocarbon (i.e., containing only carbon and hydrogen). A "hydrocarbyl group" can be acyclic or cyclic, and/or linear or branched. A "hydrocarbyl group" can include rings, ring systems, aromatic rings, and aromatic ring systems, which contain only carbon and hydrogen. "Hydrocarbyl groups" include, by way of example, aryl, alkyl, cycloalkyl, and alkylaryl/arylalkyl groups, amongst other groups as members.

When utilized herein, an "unsaturated compound" refers to, either singly or in any combination, 1,3,5-triallylisocyanurate, pentaerythritol triallyl ether, and/or a compound having formula (IV) (as defined herein). The unsaturated compounds disclosed herein have at least two carbon-carbon double bonds (e.g., two carbon-carbon double bonds, three carbon-carbon double bonds, etc.). These carbon-carbon double bonds (e.g., —C═C—), or olefinic double bonds, are non-aromatic double bonds, but the carbon-carbon double bonds can be located at any position (e.g., terminally or internally) in the unsaturated compound, unless specified otherwise or the context requires otherwise.

An aliphatic compound is an acyclic or cyclic, saturated or unsaturated compound, excluding aromatic compounds. That is, an aliphatic compound is a non-aromatic organic compound. Aliphatic compounds, and therefore aliphatic groups, can contain organic functional group(s) and/or atom(s) other than carbon and hydrogen. An "aliphatic group" is a generalized group formed by removing one or more hydrogen atoms (as necessary for the particular group) from a carbon atom of an aliphatic compound.

The term "alkyl group" is used herein in accordance with the definition specified by IUPAC: a univalent group formed by removing a hydrogen atom from an alkane. An "alkyl group" can be acyclic or cyclic, and/or linear or branched, unless otherwise specified.

A cycloalkane is a saturated cyclic hydrocarbon, with or without side chains, for example, cyclobutane and methylcyclobutane. Unsaturated cyclic hydrocarbons having one endocyclic double or one triple bond are called cycloalkenes and cycloalkynes, respectively. Those having more than one such multiple bond are cycloalkadienes, cycloalkatrienes, and so forth.

A "cycloalkyl group" is a univalent group derived by removing a hydrogen atom from a ring carbon atom from a cycloalkane. For example, a 1-methylcyclopropyl group and a 2-methylcyclopropyl group are illustrated as follows:

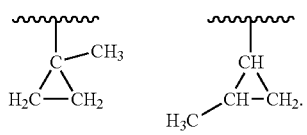

As used herein, "thiol sulfur" means sulfur from a —SH group (thiol group), while "sulfide sulfur" means sulfur from a —S— group (sulfide group). Sulfide sulfur groups encompass both intermolecular sulfide groups and intramolecular sulfide groups. The term "intermolecular sulfide" as used herein refers to sulfide bonds formed by a reaction between two molecules. The term "intramolecular sulfide" refers to sulfide bonds formed by a reaction within a single molecule.

As used herein, a "polythiol composition" refers to a composition comprising polythiol molecules. Polythiol molecules refer to molecules having two or more thiol groups per molecule (e.g., 2, 3, 4, 5, etc., thiol groups). For illustrative purposes, in addition to polythiol molecules having 2 or more SH groups, a polythiol composition also can contain compounds having only 1 thiol group. Furthermore, such polythiol compositions can contain other compounds; one non-limiting example can be the residual or unreacted unsaturated compound having 2 or more double bonds from which the polythiol composition can be derived.

In some instances, the polythiol composition can be described, while in others, the polythiol molecules (e.g., having at least 2 SH groups, having at least 3 SH groups) of the polythiol composition can be described. Consequently, within this disclosure, properties associated with polythiol compositions can include contributions from the unsaturated compound from which the compositions can be formed, as well as other reactants and by-products. In some circumstances, it can be beneficial to refer only to the polythiol molecules (e.g., having at least 2 SH groups, having at least 3 SH groups), as if the unsaturated compound, other reactants, by-products, and/or solvent are not present in the composition. Accordingly, within this disclosure, the term "polythiol molecules having at least three SH groups," used in conjunction with the polythiol composition, refers to compounds within the composition that contain at least three SH groups (e.g., these compounds can have more than three SH groups, these compounds can contain sulfide groups, etc.), and excludes any non-sulfur-containing compound (e.g., reactant unsaturated compound and/or solvent, among others), any sulfur-containing reactant (e.g., $H_2S$), and any sulfur-containing compound not having at least three SH groups. Likewise, "polythiol molecules having at least two SH groups" are interpreted in a similar manner. In sum, a polythiol composition can include all materials in a composition comprising polythiol molecules, while the polythiol molecules having at least three SH groups (or at least two SH groups) refers only to the compounds within the polythiol composition having at least three SH groups (or at least two SH groups), and these compounds additionally can have an —S— group(s) and/or more SH groups.

As utilized herein the mercaptan equivalent weight (SHEW) equals the molecular weight of a particular mercaptan molecule divided by the number of mercaptan groups in the mercaptan molecule and has the units of grams/equivalent (g/eq). When referring to a mercaptan composition which can comprises different mercaptans, the SHEW refers to an average SHEW of all the specified mercaptans in the composition.

The terms "contact product," "contacting," and the like, are used herein to describe compositions wherein the components are contacted together in any order, in any manner, and for any length of time. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a hydrocarbyl group having from 1 to 18 carbon atoms (i.e., a $C_1$-$C_{18}$ hydrocarbyl group), as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a hydrocarbyl group having 3 to 8 carbon atoms), and also including any combination of ranges between these two numbers (for example, a hydrocarbyl group having 1 to 4 carbon atoms and a hydrocarbyl group having 8 to 12 carbon atoms).

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

DETAILED DESCRIPTION OF THE INVENTION

The present invention provides polythiol compositions and methods of mercaptanizing unsaturated olefinic compounds to produce such polythiol compositions. A feature of the disclosed polythiol compositions is the presence of polythiol compounds having a —S— group (a sulfide group). Not wishing to be bound by theory, polythiol compositions containing polythiol molecules having at least two SH groups (thiol groups) and at least one sulfide group (—S— group), as described herein, can have increased mercaptan functionality, and/or increased mercaptan equivalent weight, and/or higher average molecular weight, and/or increased viscosity, and/or lower vapor pressure, and/or less objectionable odor, as compared to other polythiol compositions that contain polythiol molecules having at least two SH groups (thiol groups), but no sulfide groups (—S— groups). Moreover, the processes disclosed herein to produce such compositions are believed to be superior to other processes due to fewer process steps, reduced waste, and less burdensome purification requirements.

Polythiol Compositions Containing TMPI

Polythiol compositions consistent with embodiments of this invention disclosed and described herein can contain trismercaptopropyl isocyanurate (TMPI):

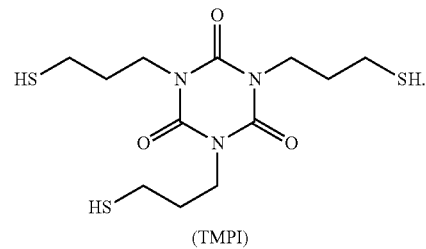 [SMILES: O=c1n(CCCS)c(=O)n(CCCS)c(=O)n1CCCS]

(TMPI)

Unless otherwise specified, the chemical structure for TMPI above, and any other structural formulas disclosed herein, whether generic or specific, are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In one embodiment, a polythiol composition can comprise polythiol molecules having the chemical structures:

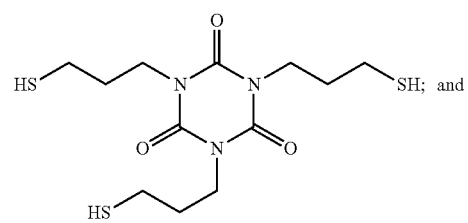

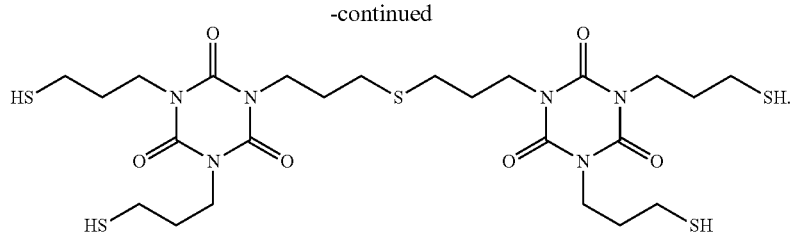

The first compound (TMPI) has three thiol groups (SH groups) and no sulfide groups, while the second compound contains four thiol groups and one intermolecular sulfide group (—S— group).

In another embodiment, a polythiol composition can comprise polythiol molecules having the following chemical structures:

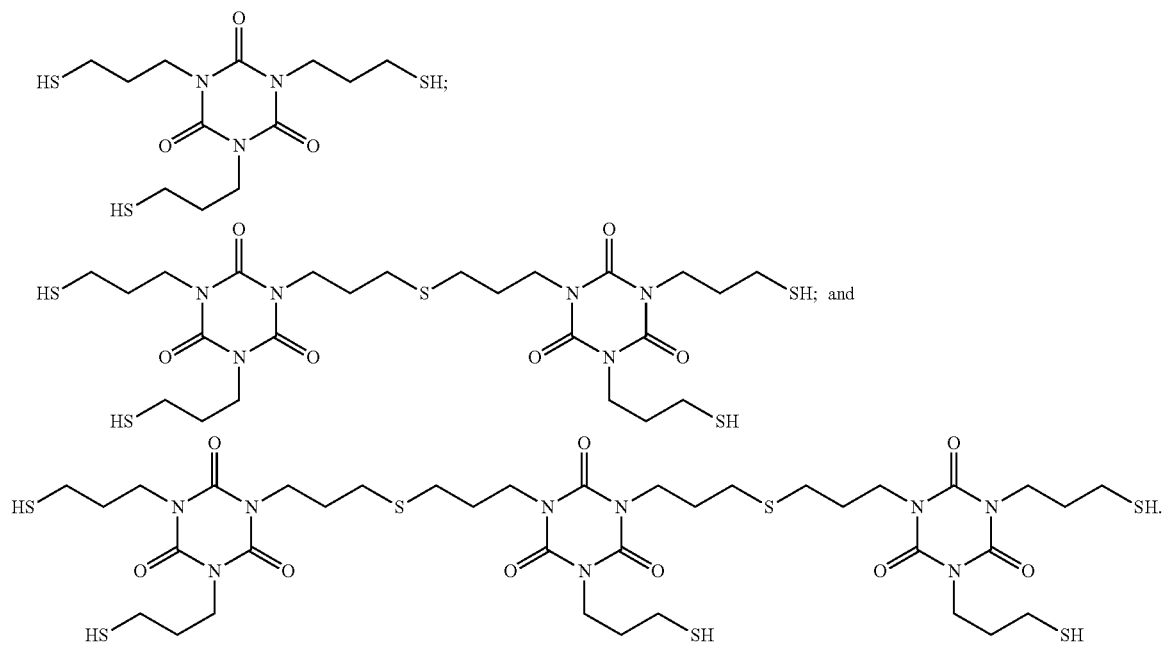

In these and other embodiments, such polythiol compositions can contain polythiol molecules having at least three SH groups. In an embodiment, the polythiol molecules having at least three SH groups can include molecules having a sulfide group (or sulfide groups). In some embodiments, the polythiol molecules having at least three SH groups can have a minimum average thiol sulfur to sulfide sulfur molar ratio of 2:1, 2.5:1, 3:1, 3.5:1, or 4:1, while in other embodiments, the polythiol molecules having at least three SH groups can have a maximum average thiol sulfur to sulfide sulfur molar ratio of 1000:1, 500:1, 250:1, 100:1, 50:1, or 25:1. As noted herein, the polythiol molecules having at least three SH groups can have a range of the average thiol sulfur to sulfide sulfur molar ratio from any minimum molar ratio disclosed herein to any maximum molar ratio disclosed herein. Accordingly, suitable ranges for the average thiol sulfur to sulfide sulfur molar ratio for the polythiol molecules having at least three SH groups can include, but are not limited to, the following: from 2:1 to 1000:1, from 2:1 to 500:1, from 2:1 to 250:1, from 3:1 to 250:1, from 2:1 to 100:1, from 3:1 to 100:1, from 4:1 to 100:1, from 2:1 to 50:1, from 2.5:1 to 50:1, from 3:1 to 50:1, from 3.5:1 to 50:1, from 4:1 to 50:1, from 2:1 to 25:1, from 3:1 to 25:1, from 4:1 to 25:1, or from 5:1 to 25:1.

The polythiol compositions can be further characterized by the amount of sulfide sulfur (sulfur from a —S— group) present in the polythiol molecules of the composition. For instance, polythiol molecules of the composition having at least three SH groups can have an average of from 0.1 mole % to 33 mole % sulfide sulfur. These percentages are based on the total sulfur content of polythiol molecules having at least three SH groups. In certain embodiments, the polythiol molecules having at least three SH groups of the polythiol composition can have a minimum average sulfide sulfur content of 0.1, 0.5, 1, 1.5, 2, 2.5, or 3 mole %, and the polythiol molecules having at least three SH groups can have a maximum average sulfide sulfur content of 33, 30, 28, 25, 20, or 15 mole %. Generally, suitable ranges for the average sulfide sulfur content for the polythiol molecules having at least three SH groups can include, but are not limited to, the following: from 0.1 to 33 mole %, from 1 to 33 mole %, from 0.1 to 30 mole %, from 0.5 to 30 mole %, from 1 to 30 mole %, from 2 to 30 mole %, from 0.1 to 25 mole %, from 1 to 25 mole %, from 1.5 to 25 mole %, from 2 to 25 mole %, from 2.5 to 25 mole %, from 3 to 25 mole %, from 1 to 20 mole %, from 2 to 20 mole %, from 3 to 20 mole %, from 1.5 to 15 mole %, or from 2.5 to 15 mole %.

Additionally or alternatively, the polythiol compositions can be further characterized by the amount of thiol sulfur (sulfur from a —SH group) present in the polythiol molecules of the composition. For example, polythiol molecules of the composition having at least three SH groups can have an average of from 67 mole % to 99 mole % thiol sulfur. These percentages are based on the total sulfur content of polythiol molecules having at least three SH groups. In particular embodiments, the polythiol molecules having at least three SH groups of the polythiol composition can have a minimum average thiol sulfur content of 67, 68, 69, 70, 72, 75, or 80 mole %, and the polythiol molecules having at least three SH groups can have a maximum average thiol sulfur content of 99, 98, 97, 96, or 95 mole %. Therefore, suitable ranges for the average thiol sulfur content for the polythiol molecules having at least three SH groups can include, but are not limited to, the following: from 67 to 99 mole %, from 70 to 99 mole %, from 75 to 99 mole %, from 80 to 99 mole %, from 67 to 98 mole %, from 68 to 98 mole %, from 72 to 98 mole %, from 75 to 98 mole %, from 67 to 97 mole %, from 69 to 97 mole %, from 72 to 97 mole %, from 75 to 97 mole %, from 80 to 97 mole %, from 90 to 97 mole %, from 68 to 95 mole %, from 75 to 95 mole %, or from 85 to 95 mole %.

Moreover, the polythiol compositions can be further characterized by the mercaptan equivalent weight (or SHEW) of the composition. In one embodiment, the minimum SHEW of polythiol molecules having at least three SH groups of the composition can be 118, 119, or 120 g/eq, while in another embodiment, the maximum SHEW of polythiol molecules having at least three SH groups of the composition can be 190, 180, or 170 g/eq. Often, the SHEW of polythiol molecules having at least three SH groups can be in the following non-limiting ranges: from 118 to 190, from 119 to 190, from 120 to 190, from 118 to 180, from 119 to 180, from 120 to 180, from 118 to 170, from 119 to 170, from 120 to 170, from 118 to 150, from 120 to 150, from 118 to 140, from 120 to 140, from 118 to 130, from 119 to 130, or from 120 to 130 g/eq.

This invention further encompasses process for producing polythiol compositions containing polythiol molecules having, for example, these chemical structures:

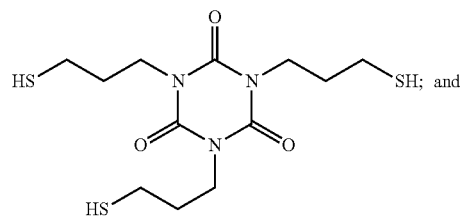

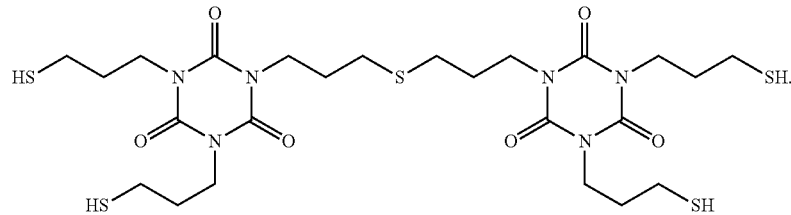

In some embodiments, the polythiol composition can include molecules having the structure:

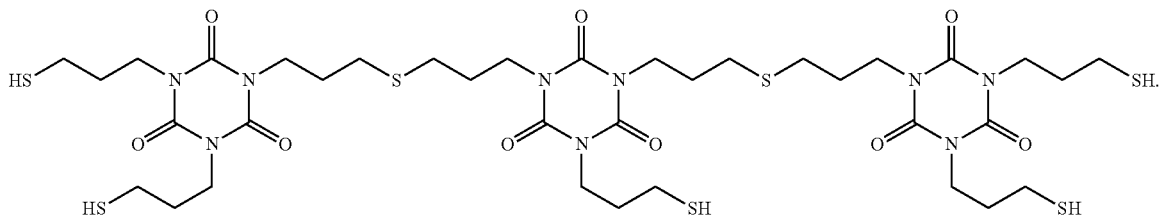 [SMILES: O=c1n(CCCS)c(=O)n(CCCSCCCn2c(=O)n(CCCS)c(=O)n(CCCSCCCn3c(=O)n(CCCS)c(=O)n(CCCS)c3=O)c2=O)c(=O)n1CCCS]

While not being limited thereto, these polythiol compositions can be produced by a process comprising contacting H$_2$S, a phosphite compound, and 1,3,5-triallylisocyanurate; and forming the polythiol composition. The molar ratio of H$_2$S to carbon-carbon double bonds of 1,3,5-triallylisocyanurate can be in a range, for example, from 5:1 to 500:1, from 5:1 to 100:1, or from 10:1 to 40:1. Additional information on processes for producing polythiol compositions is provided hereinbelow.

Polythiol Compositions Containing TMPP

Polythiol compositions consistent with certain embodiments of this invention can contain trismercaptopropyl pentaerythritol (TMPP):

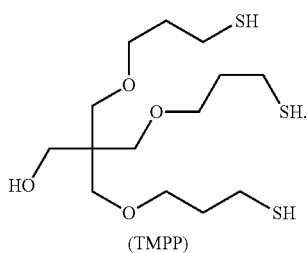 [SMILES: OCC(COCCCS)(COCCCS)COCCCS]

(TMPP)

For instance, in an embodiment, a polythiol composition can comprise polythiol molecules having the chemical structures:

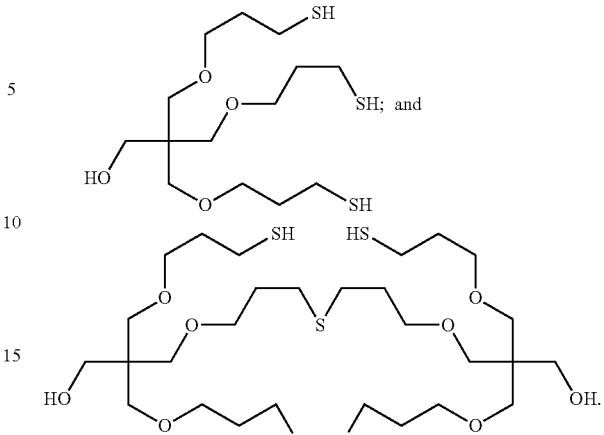

The first compound (TMPP) has three thiol groups (SH groups) and no sulfide group, while the second compound contains four thiol groups and one intermolecular sulfide group (—S— group).

In another embodiment, a polythiol composition can comprise polythiol molecules having the following chemical structures:

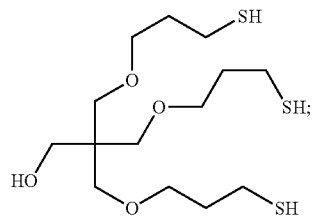

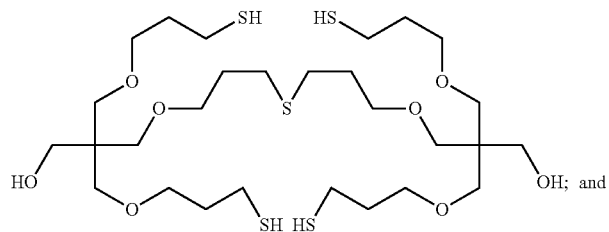

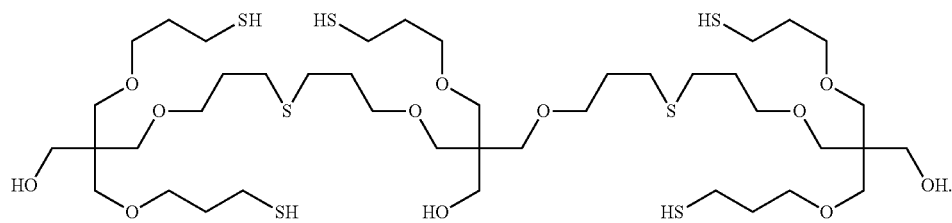 [SMILES: OCC(COCCCS)(COCCCS)COCCCSCCCOCC(CO)(COCCCS)COCCCSCCCOCC(CO)(COCCCS)COCCCS]

In these and other embodiments, such polythiol compositions can contain polythiol molecules having at least three SH groups. In an embodiment, the polythiol molecules having at least three SH groups can include molecules having a sulfide group (or sulfide groups). In some embodiments, the polythiol molecules having at least three SH groups can have a minimum average thiol sulfur to sulfide sulfur molar ratio of 2:1, 2.5:1, 3:1, 3.5:1, or 4:1, while in other embodiments, the polythiol molecules having at least three SH groups can have a maximum average thiol sulfur to sulfide sulfur molar ratio of 1000:1, 500:1, 250:1, 100:1, 50:1, or 25:1. As noted herein, the polythiol molecules having at least three SH groups can have a range of the average thiol sulfur to sulfide sulfur molar ratio from any minimum molar ratio disclosed herein to any maximum molar ratio disclosed herein. Accordingly, suitable ranges for the average thiol sulfur to sulfide sulfur molar ratio for the polythiol molecules having at least three SH groups can include, but are not limited to, the following: from 2:1 to 1000:1, from 2:1 to 500:1, from 2:1 to 250:1, from 3:1 to 250:1, from 2:1 to 100:1, from 3:1 to 100:1, from 4:1 to 100:1, from 2:1 to 50:1, from 2.5:1 to 50:1, from 3:1 to 50:1, from 3.5:1 to 50:1, from 4:1 to 50:1, from 2:1 to 25:1, from 3:1 to 25:1, from 4:1 to 25:1, or from 5:1 to 25:1.

The polythiol compositions can be further characterized by the amount of sulfide sulfur (sulfur from a —S— group) present in the polythiol molecules of the composition. For instance, polythiol molecules of the composition having at least three SH groups can have an average of from 0.1 mole % to 33 mole % sulfide sulfur. These percentages are based on the total sulfur content of polythiol molecules having at least three SH groups. In certain embodiments, the polythiol molecules having at least three SH groups of the polythiol composition can have a minimum average sulfide sulfur content of 0.1, 0.5, 1, 1.5, 2, 2.5, or 3 mole %, and the polythiol molecules having at least three SH groups can have a maximum average sulfide sulfur content of 33, 30, 28, 25, 20, or 15 mole %. Generally, suitable ranges for the average sulfide sulfur content for the polythiol molecules having at least three SH groups can include, but are not limited to, the following: from 0.1 to 33 mole %, from 1 to 33 mole %, from 0.1 to 30 mole %, from 0.5 to 30 mole %, from 1 to 30 mole %, from 2 to 30 mole %, from 0.1 to 25 mole %, from 1 to 25 mole %, from 1.5 to 25 mole %, from 2 to 25 mole %, from 2.5 to 25 mole %, from 3 to 25 mole %, from 1 to 20 mole %, from 2 to 20 mole %, from 3 to 20 mole %, from 1.5 to 15 mole %, or from 2.5 to 15 mole %.

Additionally or alternatively, the polythiol compositions can be further characterized by the amount of thiol sulfur (sulfur from a —SH group) present in the polythiol molecules of the composition. For example, polythiol molecules of the composition having at least three SH groups can have an average of from 67 mole % to 99 mole % thiol sulfur. These percentages are based on the total sulfur content of polythiol molecules having at least three SH groups. In particular embodiments, the polythiol molecules having at least three SH groups of the polythiol composition can have a minimum average thiol sulfur content of 67, 68, 69, 70, 72, 75, or 80 mole %, and the polythiol molecules having at least three SH groups can have a maximum average thiol sulfur content of 99, 98, 97, 96, or 95 mole %. Therefore, suitable ranges for the average thiol sulfur content for the polythiol molecules having at least three SH groups can include, but are not limited to, the following: from 67 to 99 mole %, from 70 to 99 mole %, from 75 to 99 mole %, from 80 to 99 mole %, from 67 to 98 mole %, from 68 to 98 mole %, from 72 to 98 mole %, from 75 to 98 mole %, from 67 to 97 mole %, from 69 to 97 mole %, from 72 to 97 mole %, from 75 to 97 mole %, from 80 to 97 mole %, from 90 to 97 mole %, from 68 to 95 mole %, from 75 to 95 mole %, or from 85 to 95 mole %.

Moreover, the polythiol compositions can be further characterized by the mercaptan equivalent weight (or SHEW) of the composition. In one embodiment, the minimum SHEW of polythiol molecules having at least three SH groups of the composition can be 120, 121, or 122 g/eq, while in another embodiment, the maximum SHEW of polythiol molecules having at least three SH groups of the composition can be 190, 180, or 170 g/eq. Often, the SHEW of polythiol molecules having at least three SH groups can be in the following non-limiting ranges: from 120 to 190, from 121 to 190, from 122 to 190, from 120 to 180, from 121 to 180, from 122 to 180, from 120 to 170, from 121 to 170, from 122 to 170, from 120 to 150, from 122 to 150, from 120 to 140, from 122 to 140, from 120 to 130, from 122 to 130, or from 125 to 150 g/eq.

This invention further encompasses process for producing polythiol compositions containing polythiol molecules having, for example, these chemical structures:

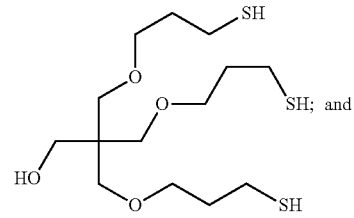

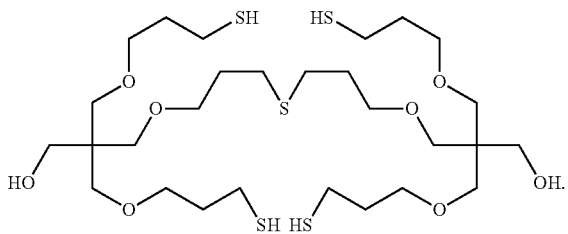

In some embodiments, the polythiol composition can include molecules having the structure:

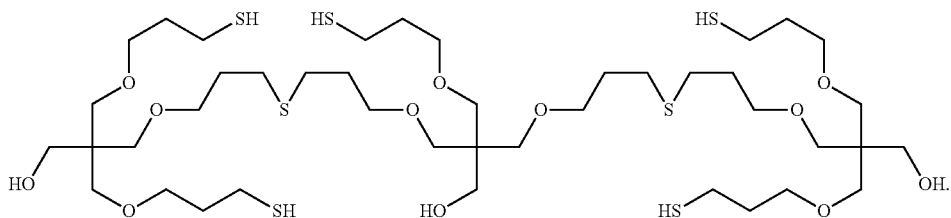

While not being limited thereto, these polythiol compositions can be produced by a process comprising contacting $H_2S$, a phosphite compound, and pentaerythritol triallyl ether; and forming the polythiol composition. The molar ratio of $H_2S$ to carbon-carbon double bonds of pentaerythritol triallyl ether can be in a range, for example, from 5:1 to 500:1, from 5:1 to 100:1, or from 10:1 to 40:1. Additional information on processes for producing polythiol compositions is provided hereinbelow.

Additional Polythiol Compositions

Additional polythiol compositions consistent with some embodiments of this invention can contain polythiol molecules having the formulas:

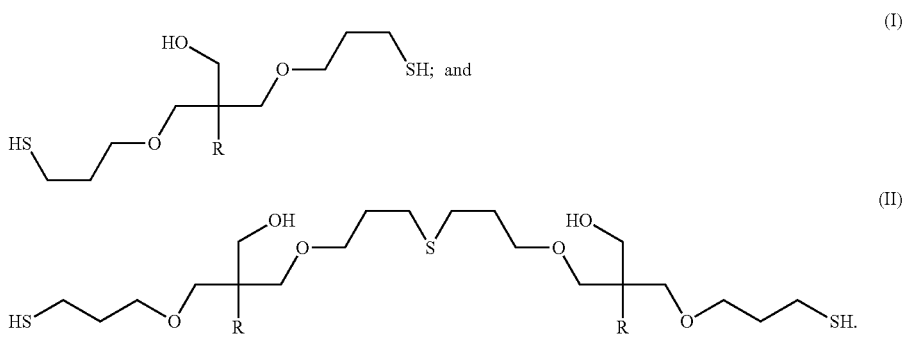

Formula (I) has thiol groups (SH groups) and no sulfide groups, while formula (II) contains two thiol groups and one intermolecular sulfide group (—S— group).

In other embodiments, polythiol compositions in accordance with embodiments of this invention can contain polythiol molecules having the following formulas:

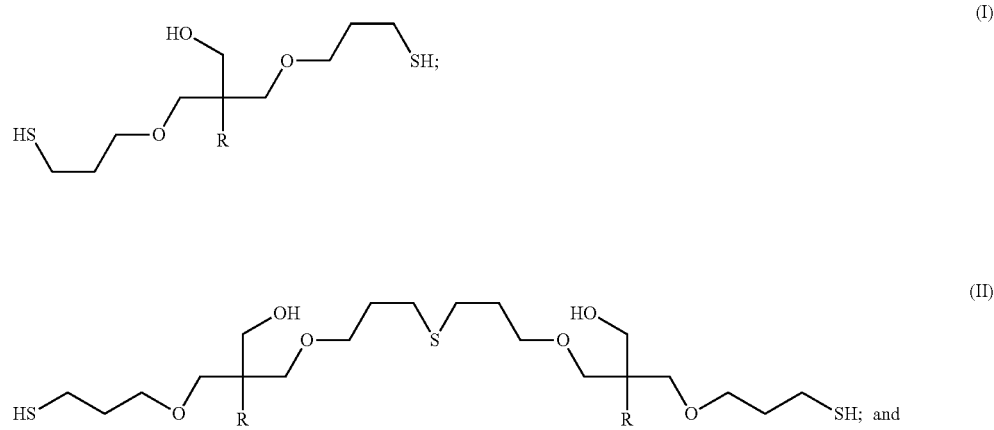

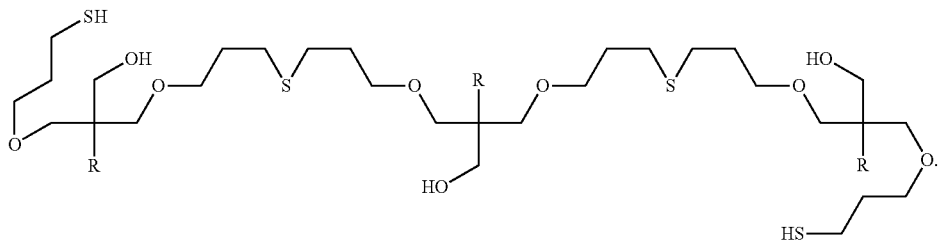

(III)

In formulas (I), (II), and (III), each R independently can be a $C_1$-$C_{18}$ hydrocarbyl group; or alternatively, a non-olefinic $C_1$-$C_{18}$ hydrocarbyl group. For instance, each R independently can be a $C_1$ to $C_{18}$ alkyl group, a $C_4$ to $C_{18}$ cycloalkyl group, a $C_6$ to $C_{18}$ aryl group, or a $C_7$ to $C_{18}$ aralkyl group; alternatively, each R independently can be a $C_1$ to $C_{12}$ alkyl group, a $C_4$ to $C_{12}$ cycloalkyl group, a $C_6$ to $C_{12}$ aryl group, or a $C_7$ to $C_{12}$ aralkyl group; alternatively, each R independently can be a $C_1$ to $C_{10}$ alkyl group, a $C_4$ to $C_{10}$ cycloalkyl group, a $C_6$ to $C_{10}$ aryl group, or a $C_7$ to $C_{10}$ aralkyl group; or alternatively, each R independently can be a $C_1$ to $C_5$ alkyl group, a $C_5$ to $C_8$ cycloalkyl group, a $C_6$ to $C_8$ aryl group, or a $C_7$ to $C_8$ aralkyl group.

Accordingly, in one embodiment, the alkyl group which can be R in formulas (I), (II), and (III) independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In another embodiment, the alkyl group which can be each R in formulas (I), (II), and (III) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In yet another embodiment, R can be an ethyl group.

Each R in formulas (I), (II), and (III) independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, each R in formulas (I), (II), and (III) can be a cyclopentyl group, a substituted cyclopentyl group, a cyclohexyl group, or a substituted cyclohexyl group. Moreover, each R can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be R in formulas (I), (II), and (III).

In some embodiments, the aryl group which can be R in formulas (I), (II), and (III) independently can be a phenyl group, a substituted phenyl group, a naphthyl group, or a substituted naphthyl group. In an embodiment, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be R in formulas (I), (II), and (III).

In some embodiments, the aralkyl group which can be the R group in formulas (I), (II), and (III) independently can be a benzyl group or a substituted benzyl group. In an embodiment, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be the R groups in formulas (I), (II), and (III).

In an embodiment, each non-hydrogen substituent(s) for the substituted cycloalkyl group, substituted aryl group, or substituted aralkyl group which can be R in formulas (I), (II), and (III) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be R in formulas (I), (II), and (III). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. Furthermore, the hydrocarbyl substituent can be a benzyl group, a phenyl group, a tolyl group, or a xylyl group.

Consistent with embodiments disclosed herein, polythiol compositions can contain polythiol molecules having formulas (I) and (II), and in further embodiments, polythiol molecules having formulas (I), (II), and (III). In these and other embodiments, such polythiol compositions can contain polythiol molecules having at least two SH groups. Polythiol molecules having formula (I) have two thiol groups (SH groups) and no sulfide group, while polythiol compounds having Formula (II) or Formula (III) contain two thiol groups and one or two (respectively) intermolecular sulfide groups (—S— groups). In some embodiments, the polythiol molecules having at least two SH groups of the polythiol composition can have a minimum average thiol sulfur to sulfide sulfur molar ratio of 1:1.5, 1:1, 2:1, or 3:1, while in other embodiments, the polythiol molecules of the polythiol composition having at least two SH groups can have a maximum average thiol sulfur to sulfide sulfur molar ratio of 1000:1, 500:1, 250:1, 100:1, 50:1, or 25:1. Accordingly, suitable ranges for the average thiol sulfur to sulfide sulfur molar ratio for the polythiol molecules having at least two SH groups can include, but are not limited to, the following: from 1:1.5 to 1000:1, from 1:1 to 500:1, from 1:1.5 to 250:1, from 1:1 to 250:1, from 1:1 to 100:1, from 3:1 to 100:1, from 1:1 to 50:1, from 2:1 to 50:1, from 3:1 to 50:1, from 5:1 to 50:1, from 1:1.5 to 40:1, from 2:1 to 40:1, from 2:1 to 25:1, from 3:1 to 25:1, from 4:1 to 25:1, or from 5:1 to 25:1.

The polythiol compositions can be further characterized by the amount of sulfide sulfur (sulfur from a —S— group) present in the polythiol molecules of the composition. For instance, polythiol molecules having at least two SH groups of the composition can have an average of from 0.1 mole % to 60 mole % sulfide sulfur. These percentages are based on the total sulfur content of polythiol molecules having at least two SH groups. In certain embodiments, the polythiol molecules having at least two SH groups of the polythiol composition can have a minimum average sulfide sulfur content of 0.1, 0.5, 1, 2, 3, or 5 mole %, and the polythiol molecules having at least two SH groups can have a maximum average sulfide sulfur content of 60, 58, 55, 45, or 40 mole %. Generally, suitable ranges for the average sulfide sulfur content for the polythiol molecules having at least two SH groups of the polythiol composition can include, but are not limited to, the following: from 0.1 to 60 mole %, from 1 to 60 mole %, from 0.1 to 55 mole %, from 0.5 to 55 mole %, from 1 to 55 mole %, from 2 to 55 mole %, from 0.1 to 45 mole %, from 1 to 45 mole %, from 2 to 45 mole %, from 3 to 45 mole %, from 5 to 45 mole %, from 1 to 40 mole %, from 3 to 40 mole %, from 5 to 40 mole %, from 5 to 30 mole %, from 10 to 40 mole %, or from 10 to 30 mole %.

Additionally or alternatively, the polythiol compositions can be further characterized by the amount of thiol sulfur (sulfur from a —SH group) present in the polythiol molecules of the composition. For example, polythiol molecules having at least two SH groups of the composition can have an average of from 40 mole % to 99 mole % thiol sulfur. These percentages are based on the total sulfur content of polythiol molecules having at least two SH groups. In particular embodiments, the polythiol molecules having at least two SH groups of the polythiol composition can have a minimum average thiol sulfur content of 40, 41, 42, 45 or 50 mole %, and the polythiol molecules having at least two SH groups can have a maximum average thiol sulfur content of 99, 98, 97, 96, or 95 mole %. Therefore, suitable ranges for the average thiol sulfur content for the polythiol molecules having at least two SH groups of the polythiol composition can include, but are not limited to, the following: from 40 to 99 mole %, from 41 to 99 mole %, from 42 to 99 mole %, from 45 to 99 mole %, from 40 to 98 mole %, from 42 to 98 mole %, from 45 to 98 mole %, from 50 to 98 mole %, from 40 to 97 mole %, from 45 to 97 mole %, from 50 to 97 mole %, from 70 to 97 mole %, from 80 to 97 mole %, from 90 to 97 mole %, from 50 to 95 mole %, from 75 to 95 mole %, or from 85 to 95 mole %.

Moreover, the polythiol compositions can be further characterized by the mercaptan equivalent weight (or SHEW) of the composition. In one embodiment, the minimum SHEW of polythiol molecules having at least two SH groups of the composition can be 142, 144, or 145 g/eq, while in another embodiment, the maximum SHEW of polythiol molecules having at least two SH groups of the composition can be 350, 300, 250, or 200 g/eq. Often, the SHEW of polythiol molecules having at least two SH groups of the composition can be in the following non-limiting ranges: from 142 to 350, from 144 to 350, from 145 to 350, from 142 to 300, from 144 to 300, from 142 to 250, from 144 to 250, from 142 to 200, from 145 to 200, from 142 to 175, from 144 to 175, from 145 to 175, from 142 to 165, from 144 to 165, from 145 to 165, or from 145 to 155 g/eq.

This invention further encompasses process for producing polythiol compositions containing polythiol molecules having, for example, formulas (I), (II), and (III). While not being limited thereto, these polythiol compositions can be produced by a process comprising contacting $H_2S$, a phosphite compound, and a compound having the formula:

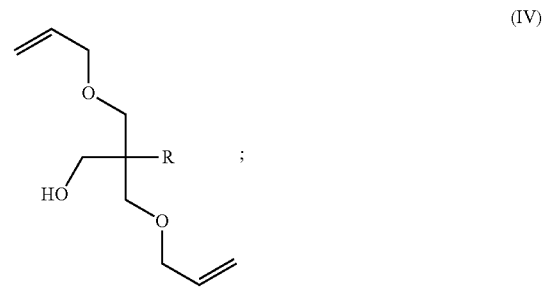

(IV)

and forming the polythiol composition. As above, R can be a $C_1$-$C_{18}$ hydrocarbyl group (e.g., an ethyl group); or alternatively, a non-olefinic $C_1$-$C_{18}$ hydrocarbyl group (e.g., an ethyl group). The molar ratio of $H_2S$ to carbon-carbon double bonds of the compound having formula (IV) can be in a range, for example, from 5:1 to 500:1, from 5:1 to 100:1, or from 10:1 to 40:1. Additional information on processes for producing polythiol compositions is provided hereinbelow.

Processes for Producing Polythiol Compositions

In accordance with certain embodiments of this invention, the disclosed polythiol compositions can be produced by a process comprising contacting $H_2S$, a phosphite compound, and an unsaturated compound (e.g., any of the unsaturated compounds disclosed herein having two carbon-carbon double bonds, three carbon-carbon double bonds, etc.); and forming the polythiol composition. In an embodiment, the unsaturated compound can be 1,3,5-triallylisocyanurate; alternatively, pentaerythritol triallyl ether; or alternatively, a compound having formula (IV). Generally, the features of the process (e.g., the unsaturated compound, the phosphite compound, the hydrogen sulfide to carbon-carbon double bond ratio, the components of and/or features of the polythiol composition, and the conditions under which the polythiol composition is formed, among others) are independently described herein and these features can be combined in any combination to further describe the disclosed process.

In some embodiments, the contacting step (step 1 of the process) can include contacting the unsaturated compound, $H_2S$, the phosphite compound, and additional unrecited materials (e.g., a solvent). In other embodiments, the contacting step can consist essentially of contacting the unsaturated compound, $H_2S$, and the phosphite compound or, alternatively, consist of contacting the unsaturated compound, $H_2S$, and the phosphite compound. Likewise, additional materials or features can be employed in the forming step (step 2 of the process). For instance, the formation of the polythiol composition can occur in the presence of ultraviolet light, discussed further hereinbelow. Moreover, it is contemplated that the processes for forming polythiol compositions can employ more than one unsaturated compound and/or more than one phosphite compound.

In the processes disclosed herein, the minimum molar ratio of $H_2S$ to carbon-carbon double bonds of the unsaturated compound can be 5:1, 10:1, 15:1, or 20:1, while the maximum molar ratio of $H_2S$ to carbon-carbon double bonds of the unsaturated compound can be 500:1, 250:1, 100:1, or 75:1. Accordingly, suitable ranges for the ratio of $H_2S$ to carbon-carbon double bonds of the unsaturated compound can include, but are not limited to, the following: from 5:1 to 500:1, from 5:1 to 250:1, from 5:1 to 100:1, from 5:1 to 75:1, from 10:1 to 500:1, from 10:1 to 100:1, from 15:1 to 500:1, from 15:1 to 250:1, from 15:1 to 150:1, from 15:1 to 75:1, from 20:1 to 100:1, from 20:1 to 75:1, from 20:1 to 50:1, from 10:1 to 40:1, from 15:1 to 45:1, or from 20:1 to 45:1.

Generally, an increase in the ratio of $H_2S$ to carbon-carbon double bonds can be used to increase the average thiol sulfur to sulfide sulfur molar ratio and/or the average thiol sulfur content of polythiol molecules in the polythiol compositions disclosed herein. In contrast, a decrease in the ratio of $H_2S$ to carbon-carbon double bonds generally can be used to increase the mercaptan equivalent weight and/or the average sulfide sulfur content of polythiol molecules in the polythiol compositions disclosed herein.

While not limited thereto, the minimum molar ratio of the phosphite compound to carbon-carbon double bonds of the unsaturated compound can be 0.0005:1, 0.001:1, 0.005:1, or 0.006:1, while the maximum molar ratio of the phosphite compound to carbon-carbon doubles bond of the unsaturated compound can be 0.1:1, 0.075:1, 0.05:1. Generally, suitable ranges for the ratio of the phosphite compound to carbon-carbon double bonds of the unsaturated compound can include, but are not limited to, the following: from 0.0005:1 to 0.1:1, from 0.0005:1 to 0.075:1, from 0.0005:1 to 0.05:1, from 0.001:1 to 0.1:1, from 0.001:1 to 0.075:1:1, from 0.001:1 to 0.05:1, from 0.005:1 to 0.1:1, from 0.005:1 to 0.05:1, from 0.006:1 to 0.001:1, from 0.006:1 to 0.05:1, from 0.008:1 to 0.05:1, from 0.008:1 to 0.04:1, from 0.01:1 to 0.1:1, or from 0.01:1 to 0.05:1.

Independently, steps 1 and 2 of the process for forming a polythiol composition can be conducted at a variety of temperatures, pressures, and time periods. For instance, the temperature at which the unsaturated compound, $H_2S$, and the phosphite compound are initially contacted can be the same as, or different from, the temperature at which the polythiol composition is formed. As an illustrative example, in step 1, the unsaturated compound, $H_2S$, and the phosphite compound can be contacted initially at temperature T1 and, after this initial combining, the temperature can be increased to a temperature T2 to allow the formation of the polythiol composition. Likewise, the pressure can be different in step 1 than in step 2. Often, the time period in step 1 is referred to as the contact time, while the time period in step 2 is referred to as the reaction time. The contact time and the reaction time can be, and usually are, different.

In an embodiment, step 1 of the process for forming a polythiol composition can be conducted at a temperature in a range from −30° C. to 120° C.; alternatively, from −30° C. to 80° C.; alternatively, from 0° C. to 100° C.; alternatively, from 20° C. to 80° C.; alternatively, from 20° C. to 50° C.; or alternatively, from 0° C. to 45° C. In these and other embodiments, after the initial contacting, the temperature can be changed, if desired, to another temperature for the formation of the polythiol composition. Accordingly, step 2 can be conducted at a temperature in a range from −30° C. to 120° C.; alternatively, from −30° C. to 80° C.; alternatively, from 0° C. to 100° C.; alternatively, from 20° C. to 80° C.; alternatively, from 20° C. to 50° C.; or alternatively, from 0° C. to 45° C. These temperature ranges also are meant to encompass circumstances where the forming step can be conducted at a series of different temperatures, instead of at a single fixed temperature, falling within the respective ranges.

In an embodiment, step 1 and/or step 2 of the process of forming a polythiol composition can be conducted at a total reactor pressure in a range from 30 to 1500 psig, such as, for example, from 50 to 1500 psig. In some embodiments, the polythiol formation in step 2 can be conducted at total reactor pressure in a range from 50 to 1500 psig; alternatively, from 50 to 1000 psig; alternatively, from 50 to 750 psig; alternatively, from 50 to 500 psig; or alternatively, from 100 to 500 psig.

The contact time in step 1 of the process is not limited to any particular range. That is, the unsaturated compound, $H_2S$, and the phosphite compound can be initially contacted rapidly, or over a longer period of time, before commencing the reaction and/or the formation of the polythiol composition in step 2. Hence, step 1 can be conducted, for example, in a time period ranging from as little as about 1-30 seconds to as long as about 1-6 hours. In some embodiments, the contact time can be in a range from 15 minutes to 3 hours, or from 30 minutes to 2 hours. The appropriate reaction time for the formation of the polythiol composition in step 2 can depend upon, for example, the reaction temperature and the molar ratios of the respective components in step 1, among other variables. However, the polythiol composition often can be formed over a time period in step 2 that can be in a range from 1 minute to 8 hours, such as, for example, from 2 minutes to 6 hours, from 5 minutes to 5 hours, from 10 minutes to 4 hours, or from 15 minutes to 3 hours.

In embodiments of this invention, once the unsaturated compound, $H_2S$, and the phosphite compound are contacted, the polythiol composition can be formed in the presence of electromagnetic radiation. For instance, the polythiol composition can be formed in the presence of ultraviolet light. Additionally or alternatively, the polythiol composition can be formed by light photolysis initiation of a free radical initiator. Additionally or alternatively, the polythiol composition can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The polythiol composition can be formed in the presence of free radicals from any one of aforementioned sources, including combinations thereof, but is not limited to free radicals generated only by these means.

In an embodiment, the step 1 contacting of the unsaturated compound, $H_2S$, and the phosphite compound can be conducted prior to the generation of free radicals and the formation of the polythiol composition in step 2.

When the polythiol composition is formed in the presence of ultraviolet light, ultraviolet light in the range, for example, from 172 to 450 nm, from 172 to 380 nm, or from 172 to 320 nm, can be employed. Ultraviolet light can be supplied from ultraviolet lamps, but other sources of ultraviolet light can be employed, and are to be considered within the scope of the present invention.

The free radical initiator can be any free radical initiator capable of forming free radicals under thermal decomposition or light photolysis. For example, the free radical initiator employed for the formation of the polythiol composition can comprise a —N=N— group, a —O—O— group, or combinations thereof; alternatively, a —N=N— group; or alternatively, a —O—O— group. Free radical initiators, therefore, can include, but are not limited to, peroxy compounds, organic azo compounds, or combinations thereof; alternatively, peroxy compounds; or alternatively, organic azo compounds. Peroxy compounds which can be utilized can include peroxides, hydroperoxides, peroxyesters, diacylperoxides, and percarbonates; alternatively, peroxides; alternatively, hydroperoxides; alternatively, peroxyesters; alternatively, diacylperoxides; or alternatively, percarbonates. In an embodiment, the peroxide can be a dialkyl peroxide. In an embodiment, the hydroperoxide can be an alkyl hydroperoxide. In an embodiment, the peroxy ester can be an alkyl peroxyalkanoate, or alternatively, an alkyl peroxyarenoate. In an embodiment, the diacylperoxide can be a diaroyl peroxide, or alternatively, a diakoyl peroxide. In an embodiment, the percarbonate can be a dihydrocarbyl percarbonate; alternatively, a diarylpercarbonate; or alternatively, a dialkylpercarbonate. Generally, the hydrocarbon and/or alkane group(s) utilized in any peroxy compound can be a $C_1$ to $C_{30}$, $C_2$ to $C_{18}$, $C_2$ to $C_{10}$, or $C_2$ to $C_5$ hydrocarbon and/or alkane group(s). Generally, the arene group utilized in any peroxy compound can be a $C_6$ to $C_{30}$, $C_6$ to $C_{18}$, $C_6$ to $C_{15}$, or $C_6$ to $C_{10}$ arene group(s). Illustrative non-limiting examples of peroxy compounds which can be utilized can include, but are not limited to, diisobutyryl peroxide, 1-(2-ethylhexanoylperoxy)-1,3-dimethylbutyl peroxypivalate, cumylperoxyneodecanoate, 1,1,3,3-tetramethylbutyl peroxyneodecanoate, t-butyl peroxyneodecanoate, 1,1,3,3-tetramethylbutyl peroxypivalate, t-butyl peroxyneoheptanoate, t-amyl peroxypivalate, t-butyl peroxypivalate, di(3,5,5-trimethylhexanoyl) peroxide, dilauroyl peroxide, didecanoyl peroxide, 2,5-dimethyl-2,5-di(2-ethylhexanoylperoxy) hexane, 1,1,3,3-tetramethylbutyl peroxy 2-ethylhexanoate, t-amyl peroxy 2-ethylhexanoate, dibenzoyl peroxide, acetyl peroxide t-butyl peroxy 2-ethylhexanoate, t-butyl peroctanoate, t-butyl peroxydiethylacetate, t-butyl peroxyisobutyrate, t-butyl peroxy 3,5,5-trimethylhexanoate, t-butyl peroxyacetate, t-butyl peoxybenzoate, 2,4-dichlorobenzoyl peroxide, t-butylpermaleic acid, di-t-butyl diperphthalate, di(4-t-butylcyclohexyl) peroxydicarbonate, di(2-ethylhexyl) peroxydicarbonate, dibutyl peroxydicarbonate, dicetyl peroxydicarbonate, dimyristyl peroxydicarbonate, t-amylperoxy 2-ethylhexyl carbonate, t-butylperoxy isopropyl carbonate, t-butylperoxy 2-ethylhexyl carbonate, 1,1-di(t-butylperoxy) 3,5,5-trimethylcyclohexane, 2,2-di(4,4-di(t-butylperoxy)cyclohexyl)propane, 1,1-di(t-butylperoxy) cyclohexane, 2,2-di(t-butylperoxy)butane, di(t-amyl) peroxide, dicumyl peroxide, di(t-butylperoxyisopropyl) benzene, 2,5-dimethyl-2,5-di(t-butylperoxy)hexane, t-butyl cumyl peroxide, 2,5-dimethyl-2,5-di(t-butylperoxy)hexyne-3, di-t-butyl peroxide, 3,6,9-triethyl-3,6,9-trimethyl-1,4,7-triperoxoane, t-butyl hydroperoxide, methyl benzyl hydroperoxide, octylperbenzoate, methyl ethyl ketone peroxide, acetone peroxide, or combinations thereof.

Non-limiting examples of suitable azo compounds include α,α'-azo diisobutyronitrile (AIBN), azobenzene, azomethane, 2,2'-azodi(2-methylbutyronitrile), 2,2'-azobis (4-methoxy-2,4-dimethyl valeronitrile), dimethyl 2,2'-azobis(2-methylpropionate), 1,1'-azobis(cyclohexane-1-carbonitrile), 1-[(cyano-1-methylethyl)azo]formamide, 2,2'-azobis(N-cyclohexyl-2-methylpropionamide), 2,2'-azobis (2,4-dimethyl valeronitrile), 2,2'-azobis(2-methylbutyronitrile), 2,2'-azobis[N-(2-propenyl)-2-methylpropionamide], 2,2'-azobis(N-butyl-2-methylpropionamide), 2,2'-azobis{2-methyl-N-[1,1-bis (hydroxymethyl)-2-hydroxyethyl]propionamide, 2,2'-azobis [2-methyl-N-(2-hydroxyethyl)propionamide], 2,2'-azobis[2-(2-imidazolin-2-yl)propane], 2,2'-azobis {2-methyl-N-[2-(1-hydroxybutyl)]propionamide}, 2,2'-azobis(2-methylpropionitrile), 4,4'-azobis(4-cyanovaleric acid), 2,2'-azobis(2-methylpropane), 2,2'-azobis(2-methylpropionamidine)dihydrochloride, methylpropionitrile, azodicarboxamide, or combinations thereof.

Generally, the peroxide and azo compound free radical initiators that can be utilized in accordance with the present invention decompose under first order kinetics. Skilled artisans can readily find the first order kinetic parameters which can be utilized to describe the decomposition of a particular free radical catalyst from sources such as chemical suppliers, industry reference publications, and/or open literature publications. Under first order kinetics, the time required for a given fraction (or percentage) of the free radical initiator to decompose, at a specific temperature, into initiating species is independent of the concentration of the free radical. This phenomenon is often stated as a half-life; that is, the time in which one-half of the free radical initiator decomposes under specific conditions (e.g., temperature). According to the first order kinetics, the half-life of a free radical initiator is defined as the time it takes one-half of the initiator to decompose at a particular temperature. Using the available first order kinetic parameters for a particular free radical initiator, the concentration of the free radical initiator present in the reaction mixture can be determined at a particular time during the reaction based upon the knowledge of the amount of free radical initiator added to the reaction, the times at which additional (if any) free radical initiator is added to the reaction, and the temperature profile of the reaction.

When the polythiol composition is formed under conditions utilizing the thermal decomposition of a free radical initiator, the polythiol composition can be formed at a temperature within a temperature range of the 1 hour half-life of the free radical initiator. Alternatively, when the polythiol composition is formed under conditions utilizing the thermal decomposition of a free radical initiator, the polythiol composition can be formed using a free radical initiator having a half-life within a time range at the temperature utilized to form the polythiol composition. For example, step 2 of the process (the formation of the polythiol composition) can be conducted at a temperature within ±25° C. of the 1 hour half-life of the free radical initiator. In other embodiments, the polythiol composition can be formed at a temperature within ±20° C. of the 1 hour half-life of the free radical initiator; alternatively, at a temperature within ±15° C. of the 1 hour half-life of the free radical initiator; alternatively, at a temperature within ±10° C. of the 1 hour half-life of the free radical initiator. In another embodiment, the polythiol composition can be formed using a free radical initiator having a half-life within a range from 0.1 to 10 hours at the temperature the polythiol composition is formed (i.e., in step 2 of the process). Alternatively, the polythiol composition can be formed using a free radical initiator having a half-life ranging from 0.1 to 10 hours, from 0.25 to 4 hours, or from 0.5 to 2 hours, at the temperature the polythiol composition is formed. As above, in some embodiments of this invention, the polythiol composition can be formed at a temperature in a range from 0° C. to 120° C.; alternatively, from 10° C. to 110° C.; alternatively, from 15° C. to 100° C.; alternatively, from 20° C. to 100° C.; alternatively, from 20° C. to 80° C.; or alternatively, from 25° C. to 80° C.

Depending upon the particular free radical initiator, a free radical initiator can produce a different number of free radical reaction-initiating species per mole of free radical initiator; thus, the concentration of the free radical initiator can be stated in terms which describe the number of free radical reaction-initiating species generated per mole of free radical initiator. The term "equivalent" is often used to describe the number of reaction-initiating species produced per mole of free radical initiator. For example, one skilled in the art will readily recognize that di-t-butylperoxide can generate two free radical reaction-initiating species per mole of di-t-butylperoxide, while 2,5-bis(t-butylperoxy)-2,5-dimethylhexane can generate four free radical reaction-initiating species per mole of 2,5-bis(t-butylperoxy)-2,5-dimethylhexane.

In some embodiments, a photoinitiator can be utilized. Commercially available photoinitiators include, by way of example, Irgacure® 184 (1-hydroxy-cyclohexyl-phenyl-ketone), Irgacure® 500 (50% 1-hydroxy-cyclohexyl-phenyl-ketone and 50% benzophenone), Irgacure® 819 (Bis-(2,4,6-trimethylbenzoyl)-phenylphosphineoxide), and Irgacure® 127 (2-hydroxy-1-{4-[4-(2-hydroxy-2-methyl-propionyl)-benzyl]-phenyl}-2-methyl-propan-1-one), all available from Ciba Specialty Chemicals, and Duracure 1173 (2-hydroxy-2-methyl-1-phenyl-1-propanone).

When a free radical initiator is present in step 1 and/or in step 2 of the process, the weight percentage of the free radical initiator, based on the weight of the unsaturated compound, can be in a range from 0.05 to 10 wt. %, from 0.1 to 9 wt. %, from 0.2 to 5 wt. %, or from 0.1 to 2 wt. %. When a photoinitiator is present in step 1 and/or in step 2 of the process, the weight percentage of the photoinitiator, based on the weight of the unsaturated compound, can be in a range from 0.01 to 5 wt. %, from 0.05 to 5 wt. %, from 0.5 to 3 wt. %, or from 1 to 4 wt. %. Other amounts of the free radical initiator and/or the photoinitiator can be employed depending on the specific process conditions used to form the polythiol composition (e.g., temperature, pressure, time) and the respective ratios of $H_2S$ to unsaturated compound and of phosphite compound to unsaturated compound, amongst other factors. It is contemplated that more than one free radical initiator, more than one photoinitiator, or combinations of free radical initiator(s) and photoinitiator(s), can be employed.

In an embodiment, the polythiol composition can be formed in the absence of a solvent. However, in other embodiments, the polythiol can be formed in the presence of a solvent. Typically, when used, the solvent can be present in an amount up to 1,000 wt. %, based on the weight of the unsaturated compound. Alternatively, the formation of the polythiol can be performed in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent utilized can be at least 5 wt. %, at least 10 wt. %, at least 25 wt. %, at least 50 wt. %, or at least 75 wt. %, based on the weight of the unsaturated compound. Generally, the range of solvent which can be utilized can range from any minimum amount of solvent disclosed herein to any maximum amount of solvent disclosed herein. In some non-limiting embodiments, the formation of the polythiol can be performed in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the unsaturated compound. The organic solvent can be contacted with the unsaturated compound, $H_2S$, and the phosphite compound in step 1 of the process, and remain present during the formation of the polythiol composition. Alternatively, the organic solvent can be added after the initial contacting in step 1. Organic solvents which can be utilized as the solvent are described herein, and these organic solvents can be utilized without limitation in the processes described herein.

In the processes for producing a polythiol composition disclosed herein, it is contemplated that at least 60% of the carbon-carbon double bonds of the unsaturated compound can react to form a sulfur-containing group in the polythiol composition. Often, at least 65% of the carbon-carbon double bonds of the unsaturated compound can react to form a sulfur-containing group; alternatively, at least 70%; alternatively; at least 75%; alternatively, at least 80%; alternatively, at least 85%; alternatively, at least 90%; alternatively, at least 95%; alternatively, at least 98%; or alternatively, at least 99%.

Once formed, the polythiol composition, or specific fractions of the polythiol composition, can be purified and/or isolated and/or separated using suitable techniques which include, but are not limited to, evaporation, distillation, crystallization, extraction, washing, decanting, filtering, drying, including combinations of more than one of these techniques. In one embodiment, the process for producing a polythiol composition can further comprise a step of separating or removing at least a portion of the $H_2S$, of the phosphite compound, of the unsaturated compound, of compounds having only one sulfur atom if the unsaturated compound has two carbon-carbon double bonds (or of compounds having only one or two sulfur atoms if the unsaturated compound has three carbon-carbon double bonds), or any combination thereof, from the polythiol composition. For instance, these materials can be separated or removed by distillation, by short path distillation, by wiped film evaporation, or by a combination of these techniques.

Phosphite Compounds

Generally, the phosphite compound employed in the processes for forming a polythiol composition disclosed herein can comprise, consist essentially of, or consist of, a compound having the formula:

$$P(OR^1)_3.$$

In this formula, each $R^1$ independently can be a $C_1$-$C_{18}$ hydrocarbyl group; alternatively, a $C_1$-$C_{10}$ hydrocarbyl group; alternatively, a $C_1$-$C_5$ hydrocarbyl group; alternatively, a $C_1$-$C_{18}$ alkyl group; alternatively, a $C_1$-$C_{10}$ alkyl group; alternatively, a $C_1$-$C_5$ alkyl group; alternatively, a $C_6$-$C_{18}$ aryl group; or alternatively, a $C_6$-$C_{10}$ aryl group. Accordingly, each $R^1$ independently can be a methyl group, an ethyl group, a propyl group, a butyl group, a pentyl group, a hexyl group, a heptyl group, an octyl group, a nonyl group, or a decyl group; alternatively, $R^1$ can be a methyl group, an ethyl group, a propyl group, a butyl group, or a pentyl group; alternatively, $R^1$ can be a methyl group; alternatively, $R^1$ can be an ethyl group; alternatively, $R^1$ can be a propyl group; alternatively, $R^1$ can be a butyl group; alternatively, $R^1$ can be a pentyl group; alternatively, $R^1$ can be a hexyl group; alternatively, $R^1$ can be a heptyl group; alternatively, $R^1$ can be an octyl group; alternatively, $R^1$ can be a nonyl group; or alternatively, $R^1$ can be a decyl group. In some embodiments, each $R^1$ independently can be a phenyl group, a tolyl group, a xylyl group, or a naphthyl group; alternatively, a phenyl group, a tolyl group, or a xylyl group; alternatively, a phenyl group, a tolyl group; alternatively, a xylyl group; or alternatively, a naphthyl group.

In accordance with an embodiment of this invention, the phosphite compound can comprise, consist essentially of, or consist of, a trialkylphosphite, or alternatively, a triarylphosphite. In accordance with another embodiment of this invention, the phosphite compound can comprise, consist essentially of, or consist of, trimethylphosphite, triethylphosphite, tributylphosphite, or combinations thereof. Yet, in accordance with another embodiment of this invention, the phosphite compound can comprise trimethylphosphite; alternatively, triethylphosphite; or alternatively, tributylphosphite. In another embodiment, the phosphite compound can comprise, consist essentially of, or consist of, triphenylphosphite.

Solvents

As described above, the polythiol composition can be formed in the presence of a solvent. The solvent can comprise, consist essentially of, or consist of, a hydrocarbon, an aromatic hydrocarbon, a ketone, an alcohol, an ether, or combinations thereof. Hence, mixtures and/or combinations of solvents can be utilized in the processes of forming polythiol compositions disclosed herein.

In an embodiment, the solvent employed in forming the polythiol composition can comprise, consist essentially of, or consist of, a hydrocarbon solvent. Suitable hydrocarbon solvents can include, for example, aliphatic hydrocarbons, petroleum distillates, or combinations thereof. Aliphatic hydrocarbons which can be useful as the solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic, and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

In an embodiment, the solvent employed in forming the polythiol composition can comprise, consist essentially of, or consist of, an aromatic hydrocarbon solvent. Aromatic hydrocarbons can include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

In an embodiment, the solvent employed in forming the polythiol composition can comprise, consist essentially of, or consist of, a ketone solvent, an alcohol solvent, an ether solvent, or combinations thereof; alternatively, a ketone solvent; alternatively, an alcohol solvent; or alternatively, an ether solvent. Suitable ketones, alcohols, or ethers include $C_2$ to $C_{20}$ ketones, alcohols, or ethers; alternatively, $C_2$ to $C_{10}$ ketones, alcohols, or ethers; or alternatively, $C_2$ to $C_5$ ketones, alcohols, or ethers. Non-limiting examples of suitable ketone solvents can include acetone, ethyl methyl ketone, and combinations thereof. Non-limiting examples of suitable alcohol solvents can include methanol, ethanol, propanol, isopropanol, n-butanol, isobutanol, pentanol, hexanol, heptanol, octanol, benzyl alcohol, phenol, cyclohexanol, or combinations thereof. Suitable ether solvents can be cyclic or acyclic, non-limiting examples of which can include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, substituted 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Articles

The polythiol compositions disclosed herein can be used as curing agents for epoxy and urethane coatings, paints, adhesives, and other articles. For instance, the coatings and adhesives can be used with metal (e.g., aluminum, steel, copper, etc.), wood, glass, ceramic, and plastic substrates, including combinations of these substrates.

Formulations containing the polythiol compositions can contain other additives or components depending upon the desired properties and end-use application. These additives or components can include, but are not limited to, catalysts, solvents/diluents, plasticizers, fillers, fibers, pigments/colorants, pigment dispersing agents, flow modifiers, surface modifiers, antioxidants or stabilizers, or combinations thereof.

It is contemplated that formulations, coatings, adhesives, and other articles that contain and/or are produced from the polythiol compositions disclosed herein can have lower levels of offensive or objectionable odor, as compared to compositions produced by other processes of producing polythiol compositions.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The polythiol compositions were produced in accordance with the following procedure. Either a 5-L or a 379-L (100-gallon) ultraviolet light reactor was used for each example; working volumes were 4 L and 80 gallon, respectively. The 5-L stainless-steel reactor had a quartz lamp well mounted horizontal to an off-set stir shaft. The reactors were equipped with a thermowell, cooling coils, a charge port, a sample port, and a bottom drain valve. To the respective reactor, the desired unsaturated compound (e.g., TMPDAE, PTAE, TAIC), the desired amount of phosphite compound, free radical initiator (if utilized), photoinitiator (if utilized), and solvent (if utilized) were charged to the reactor through the charge port. The reactor was sealed and pressure checked with nitrogen at 450 psig. The reactor was vented and the desired amount of $H_2S$ was charged to the reactor; the operating pressure was generally between 235 and 400 psig. The reactor contents were heated and controlled by setting the external circulating bath at the desired temperature of about 25-35° C. The 379-L reactor had the quartz lamp and lamp well mounted vertically in an external pipe. Reagents were charged to the 379-L reactor and the fluid was pumped up-flow through the external pipe with the lamp well and back into the 379-L reactor.

The reaction mixture was allowed to mix for 15 to 30 minutes. After this mixing period, the ultraviolet lamp was turned on. The ultraviolet lamp typically required 3 to 7 minutes to reach full power. The ultraviolet lamp power was 100 watts for the 5-L reactor, and 7.5 kW for the 379-L reactor.

When the conversion of carbon-carbon double bonds was complete or the desired reaction time was reached, the ultraviolet lamp was turned off. The $H_2S$ was then slowly vented from the reactor. For the 5-L reactor, the reactor was purged with nitrogen and the contents were drained via a bottom drain valve. The reaction product was placed in a rotoevaporator at 60° C. and low vacuum to remove additional residual $H_2S$ and other light materials (e.g., solvent). For the 379-L reactor, the reactor was vented to the flare line and then further degassed. The light ends for the 379-L reactor material were stripped using a wiped film evaporator. The crude reactor product was analyzed using Gas Chromatography (GC). GC analysis of the sulfur-containing compounds excluded peaks attributed to phosphorus-containing materials. Product composition information based upon GC data is presented in area percentages, unless otherwise specified. Weight percentage of thiol sulfur (Wt. % SH) was determined by iodine titration, and weight percentage of total sulfur (Wt. % Total S) was determined by x-ray. Mercaptan equivalent weight (SHEW) in Table II and Table IV that follow is the grams of mercaptan sulfur (thiol sulfur) per equivalent (g/eq) of the polythiol composition. SHEW is equal to the average molecular weight (g/mol) of the polymercaptan divided by SH functionality, and it also can be calculated as follows: SHEW=(32.06 grams mercaptan sulfur/equivalent)/(wt. % SH/100), where wt. % SH=grams thiol sulfur (or mercaptan sulfur) per gram of the polythiol composition.

In some examples, a wiped film evaporator (WFE) was utilized. The wiped film evaporator was run under standard operating procedures, with a wall temperature of the vessel (glass) in the 100-140° C. range, and pressure in the 1-2 torr range. The wiper blades typically operated at 200-300 rpm. The rate of addition of the incoming product was in the 50-300 cc/hr range. Operating conditions varied depending on the volatility of the material(s) to be removed, among other factors.

Molecular weight data were obtained using an Agilent HP1100 Isocratic HPLC thermostatted autosampler system with control module using PolymerLabs Cirrus software to control the system and for data processing. An Agilent 1100 series RI detector was used with solvent degassing. The columns used were PLgel Minimix E columns from PolymerLabs. The solvent used was tetrahydrofuran (THF), and samples were approximately 0.5% w/w in THF. The column temperature was 40° C. and refractive index detector was set at 35° C. The injection volume was 20 µL. Flow rate was 0.3 mL/min and run time was about 26 min. Two polystyrene standard sets were used having the following molecular weights (g/mol): standard set 1 (20020, 4910, 1200, 92) and standard set 2 (38640, 10730, 2340, 480, 266, 92). Both sets of standards were used for each sample.

Examples 1-9

Polythiol Compositions Produced from Trimethylolpropanediallylether (TMPDAE)

Table I summarizes certain process conditions and analytical results for the polythiol compositions of Examples 1-9. The following abbreviations and conventions are used in Table I: TMPDAE is trimethylolpropanediallylether; BMPT is bismercaptopropyl trimethylolpropane; TEP is triethylphosphite; Irg 500 is Irgacure® 500; $H_2S$ Molar Ratio is Moles of $H_2S$/moles of carbon-carbon double bonds of TMPDAE; and weight and mole percentages of TEP and Irg 500 are based on the amount of TMPDAE. The % conversion is based on the number of double bonds of TMPDAE that have reacted, determined using Raman spectroscopy. The % TMPDAE, % mono-S, % BMPT, and % Sulfide were determined using gas chromatography, where % TMPDAE equals the amount of residual TMPDAE; % mono-S equals the amount of compounds having one sulfur atom; % BMPT equals the amount of bismercaptopropyl trimethylolpropane; and % Sulfide equals the amount of compounds having at least one sulfide sulfur. Wt. % SH is the total amount of thiol sulfur in the composition, and Wt. % Total S is the total amount of sulfur in the composition.

The compositions of Examples 1-6 were analyzed prior to WFE and, therefore, contain polythiol molecules having less than two SH groups. Example 7 was a composition prepared after the composition of Example 6 was subjected to WFE. Example 8 was a mixture of various laboratory produced thiol compositions, and Example 9 was a composition prepared after the composition of Example 8 was subjected to WFE.

FIG. 1 is a plot illustrating the respective amount of material versus the logarithm of molecular weight for TMPDAE and for the polythiol composition of Example 9 containing BMPT. The largest peak at the lower molecular weight is the reactant, TMPDAE. The curve for the composition of Example 9 has three definitive peaks to the right of (i.e., at a higher molecular weight than) TMPDAE. The first and larger peak is BMPT (relative area of 83.3%). The peaks at the higher molecular weights are indicative of a polythiol molecule having one intermolecular sulfide (relative area of 13.9%), and a polythiol molecule having two intermolecular sulfides (relative area of 2.7%), respectively. The structures for these molecules are provided below:

Examples 10-14

Polythiol Compositions Produced from Pentaerythritol Triallyl Ether (PTAE)

Table II summarizes certain process conditions and analytical results for the polythiol compositions of Examples 10-14. The following abbreviations and conventions are used in Table II: PTAE is pentaerythritol triallyl ether; TEP

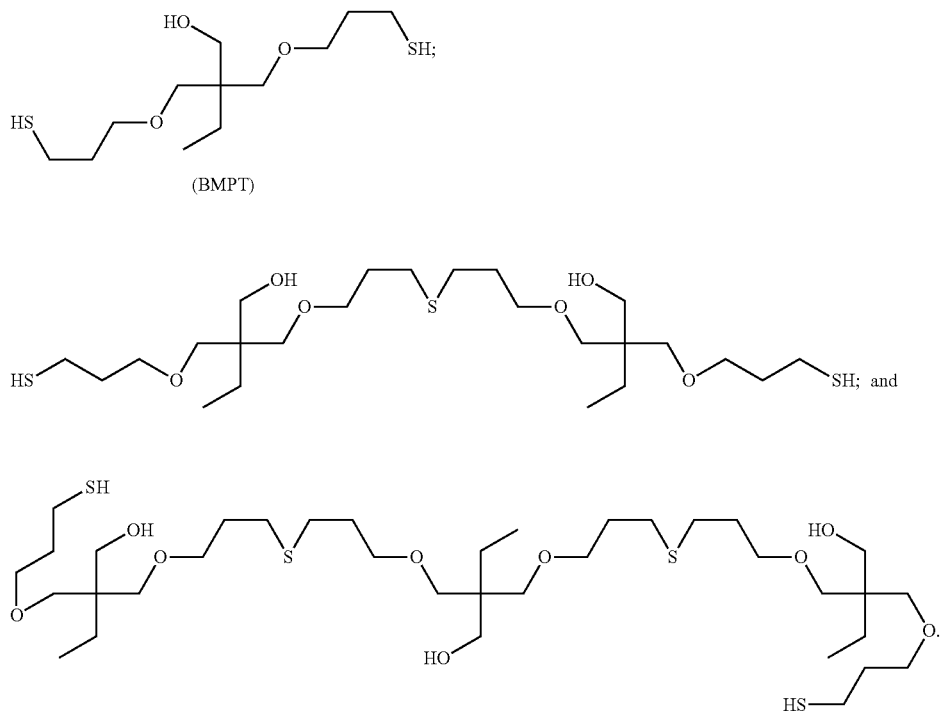

(BMPT)

TABLE I

Polythiol Compositions of Examples 1-9.

| Example Number | 1 | 2 | 3 | 4 | 5 | 6 | 7 | 8 | 9 |
|---|---|---|---|---|---|---|---|---|---|
| Reactor | 5-L | 5-L | 5-L | 5-L | 5-L | 379-L | Ex. 6 After WFE | 5-L Mix | Ex. 8 After WFE |
| Weight TMPDAE (g) | 301 | 301 | 301 | 301 | 602 | $2.54 \times 10^4$ | | | |
| Weight H$_2$S (g) | 2900 | 2900 | 2900 | 2900 | 2600 | $2.18 \times 10^5$ | | | |
| Weight TEP (g) | 1.5 | 0.5 | 0.1 | 0.3 | 5 | $1.27. \times 10^2$ | | | |
| Weight Irg 500 (g) | 0.5 | 0.5 | 0.1 | 0.3 | 0.5 | $4.08 \times 10^1$ | | | |
| H$_2$S Molar Ratio | 30 | 30 | 30 | 30 | 14 | 27 | | | |
| Reaction Time (min) | 10 | 10 | 150 | 60 | 120 | 30 | | | |
| % Conversion | 99 | 99 | 82 | 76 | 100 | >98 | | | |
| Wt. % TEP | 0.50 | 0.17 | 0.033 | 0.1 | 0.83 | 0.50 | | | |
| Wt. % Irg 500 | 0.17 | 0.17 | 0.033 | 0.1 | 0.083 | 0.16 | | | |
| Moles TMPDAE | 1.40 | 1.40 | 1.40 | 1.40 | 2.81 | 0.261 | | | |
| Olefin equivalents | 2.81 | 2.81 | 2.81 | 2.81 | 5.62 | 0.523 | | | |
| Moles TEP | 0.00903 | 0.00301 | 0.00060 | 0.00181 | 0.0301 | 0.00169 | | | |
| Moles Irg 500 | 0.00269 | 0.00269 | 0.00054 | 0.00161 | 0.00269 | 0.00048 | | | |
| Mole % TEP | 0.321 | 0.107 | 0.021 | 0.064 | 0.536 | 0.322 | | | |
| Mole % Irg 500 | 0.096 | 0.096 | 0.019 | 0.057 | 0.048 | 0.093 | | | |
| Wt. % SH | 21.04 | 21.48 | 18.49 | — | 21.10 | 20.71 | 20.86 | — | 20.66 |
| Wt. % Total S | 21.92 | 21.88 | 19.08 | — | 21.67 | 21.47 | 21.66 | — | 21.87 |
| % TMPDAE | 0.73 | 0.96 | 4.78 | — | 0.0 | <0.2 | 0.0 | 0.30 | 0.0 |
| % mono-S | 4.50 | 6.22 | 29.35 | — | 6.48 | 11.2 | 4.90 | 4.10 | 2.50 |
| % BMPT | 84.47 | 86.76 | 58.86 | — | 87.00 | 81.4 | 80.90 | 80.80 | 81.60 |
| % Sulfide | 10.30 | 6.06 | 7.01 | — | 6.52 | 7.20 | 14.20 | 14.80 | 15.90 | is triethylphosphite; Irg 500 is Irgacure® 500; $H_2S$ Molar Ratio is Moles of $H_2S$/moles of carbon-carbon double bonds of PTAE; and weight and mole percentages of TEP and Irg 500 are based on the amount of PTAE. The % conversion is based on the number of double bonds of PTAE that have reacted. Wt. % SH is the total amount of thiol sulfur in the composition, and Wt. % Total S is the total amount of sulfur in the composition. SHEW is the mercaptan equivalent weight (g/eq).

The compositions of Examples 10 and 12-14 were analyzed prior to WFE and, therefore, contain polythiol molecules having less than three SH groups. Example 11 was a composition prepared after the composition of Example 10 was combined with other similar laboratory preparations, and then subjected to WFE.

Figure 2:
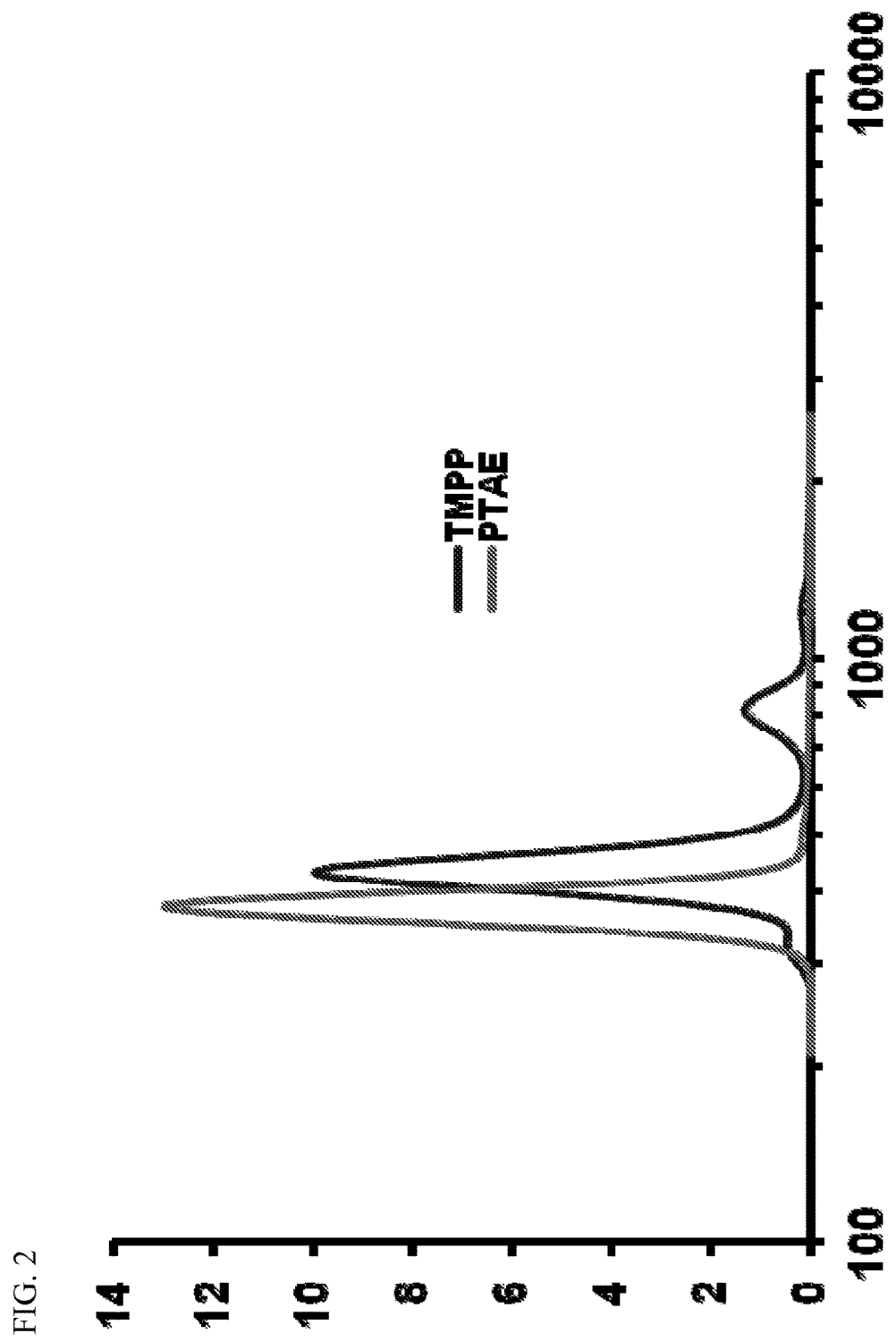
FIG. 2 presents a plot of the molecular weight distributions of PTAE and the polythiol composition of Example 11 containing TMPP.

FIG. 2 is a plot illustrating the respective amount of material versus the logarithm of molecular weight for PTAE and for the polythiol composition of Example 11 containing TMPP. The largest peak at the lower molecular weight is the reactant, PTAE. The curve for the composition of Example 11 has three definitive peaks to the right of (i.e., at a higher molecular weight than) PTAE. The first and larger peak is TMPP (relative area of 86.8%). The peaks at the higher molecular weights are indicative of a polythiol molecule having one intermolecular sulfide (relative area of 11.8%), and a polythiol molecule having two intermolecular sulfides (relative area of 1.4%), respectively. The structures for these molecules are provided below:

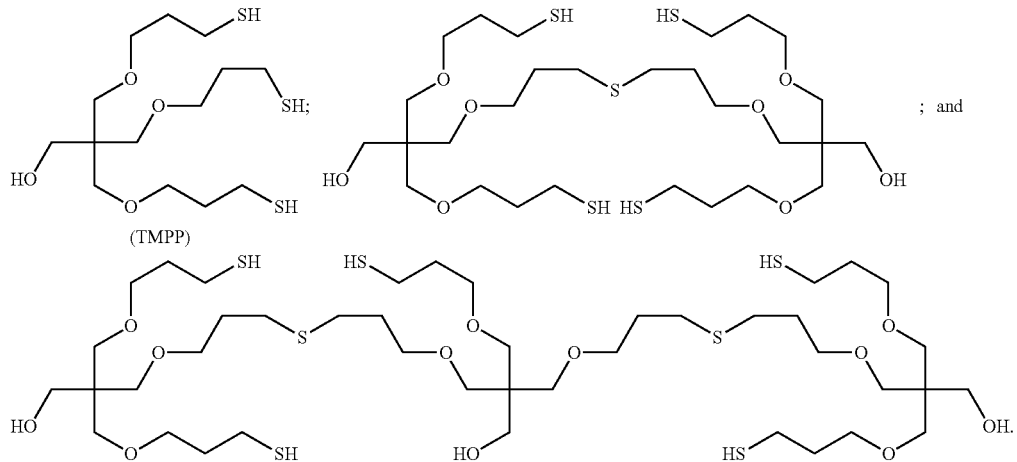

(TMPP)

TABLE II

Polythiol Compositions of Examples 10-14

| | Example Number | | | | |
|---|---|---|---|---|---|
| | 10 | 11 | 12 | 13 | 14 |
| Reactor | 5-L | Ex. 10 After WFE | 5-L | 5-L | 5-L |
| Weight PTAE (g) | 243 | | 245 | 243 | 243 |
| Weight $H_2S$ (g) | 3000 | | 3000 | 3000 | 3000 |
| Weight TEP (g) | 6 | | 18 | 10 | 6 |
| Weight Irg 500 (g) | 0 | | 1 | 0 | 0 |
| $H_2S$ Molar Ratio | 31 | | 31 | 30 | 30 |
| Reaction Time (min) | <10 | | <10 | 13 | <15 |
| % Conversion | 100 | | 100 | >99 | >99 |
| Wt. % TEP | 2.5 | | 7.3 | 4.1 | 2.5 |

TABLE II-continued

Polythiol Compositions of Examples 10-14

| | Example Number | | | | |
|---|---|---|---|---|---|
| | 10 | 11 | 12 | 13 | 14 |
| Wt. % Irg 500 | 0 | | 0.4 | 0 | 0 |
| Moles PTAE | 0.95 | | 0.96 | 0.95 | 0.95 |
| Olefin equivalents | 2.84 | | 2.87 | 2.85 | 2.85 |
| Moles TEP | 0.0361 | | 0.1083 | 0.0602 | 0.0361 |
| Moles Irg 500 | 0 | — | | 0 | 0 |
| Mole % TEP | 1.27 | | 3.78 | — | 1.27 |
| Mole % Irg 500 | 0 | — | | 0 | 0 |
| Wt. % SH | 24.15 | 24.34 | 24.30 | 25.2 | 24.4 |
| Wt. % Total S | — | 25.81 | 25.59 | — | — |
| SHEW (g/eq) | | | | 127.2 | 131.4 |

Examples 15-29

Polythiol Compositions Produced from 1,3,5-triallylisocyanurate (TAIC)

Table III and Table IV summarize certain process conditions and analytical results for the polythiol compositions of Examples 15-21 and Examples 22-29, respectively. The following abbreviations and conventions are used in Tables III-IV:

TAIC is 1,3,5-triallylisocyanurate; TMPI is trismercaptopropyl isocyanurate; TEP is triethylphosphite; Irg 500 is Irgacure® 500; $H_2S$ Molar Ratio equals Moles of $H_2S$/moles of carbon-carbon double bonds of TAIC; and weight and mole percentages of TEP and Irg 500 are based on the amount of TAIC. The % conversion is based on the number of double bonds of TAIC that have reacted. The % mono-S, % DiS, % TMPI, and % Heavies were determined using gas chromatography, where % mono-S equals the amount of compounds having one sulfur; % Di-S equals the amount of compounds having two sulfurs; % TMPI equals the amount of trismercaptopropyl isocyanurate; and % Heavies equals the amount of compounds having at least one sulfide group. Wt. % SH is the total amount of thiol sulfur in the composition, and Wt. % Total S is the total amount of sulfur in the composition. SHEW is the mercaptan equivalent weight (g/eq).

The compositions of Examples 15-20 and 22-29 were analyzed prior to WFE and, therefore, contain polythiol molecules having less than three SH groups. Example 21 was a composition prepared after the composition of Example 20 was subjected to WFE. The GC data in Table III does not show all of the heavier compounds of the respective compositions. The Wt. % SH values for Examples 25-27 and 29 listed in Table IV are artificially high due to errors in the analytical testing procedure.

Figure 3:
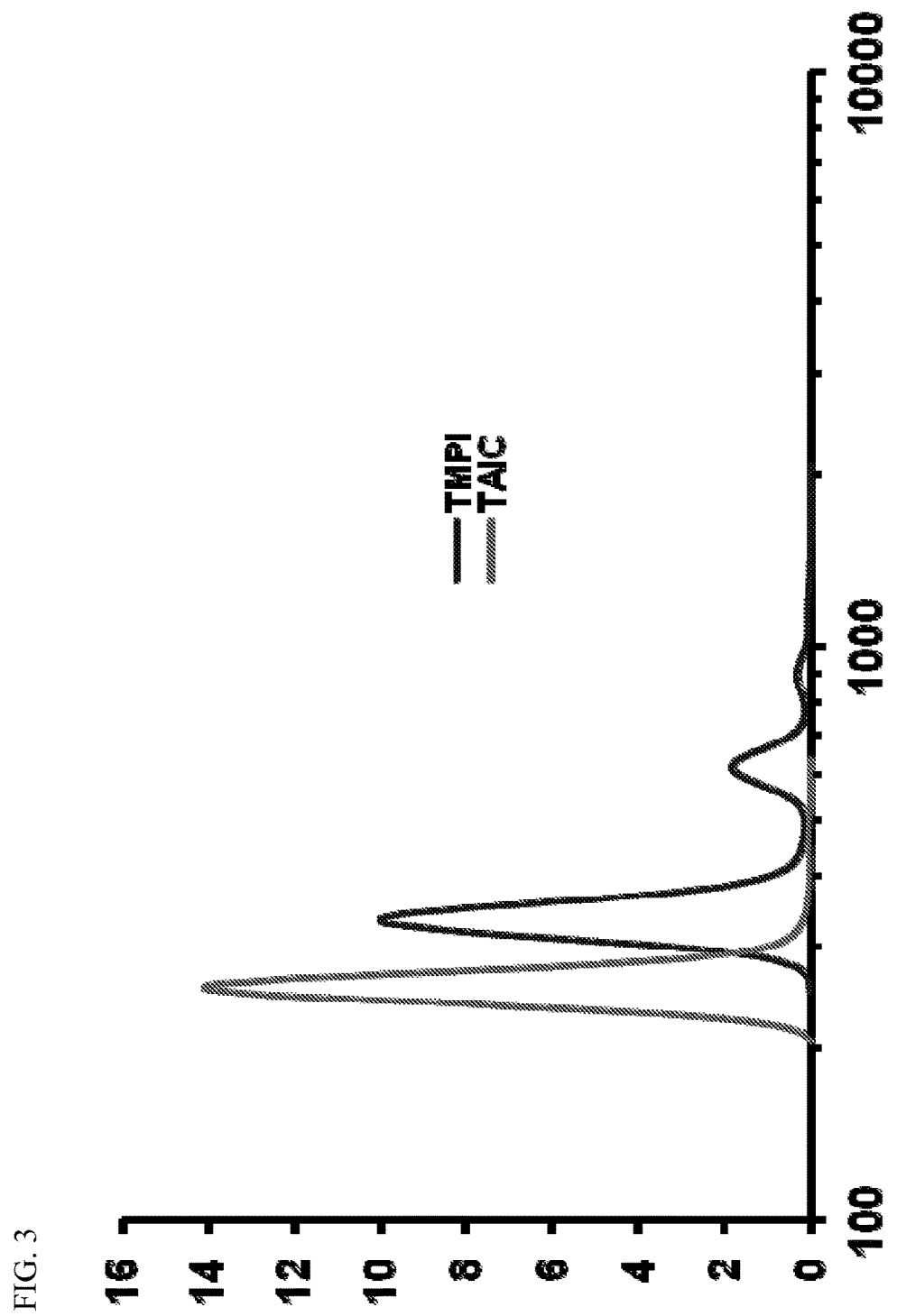
FIG. 3 presents a plot of the molecular weight distribution of TRIC and the polythiol composition of Example 21 containing TMPI.

FIG. 3 is a plot illustrating the respective amount of material versus the logarithm of molecular weight for TAIC and for the polythiol composition of Example 21 containing TMPI. The largest peak at the lower molecular weight is the reactant, TRIC. The curve for the composition of Example 21 has three definitive peaks to the right of (i.e., at a higher molecular weight than) TAIC. The first and larger peak is TMPI (relative area of 84.4%). The peaks at the higher molecular weights are indicative of a polythiol molecule having one intermolecular sulfide (relative area of 12.7%), and a polythiol molecule having two intermolecular sulfides (relative area of 2.3%), respectively. The structures for these molecules are provided below:

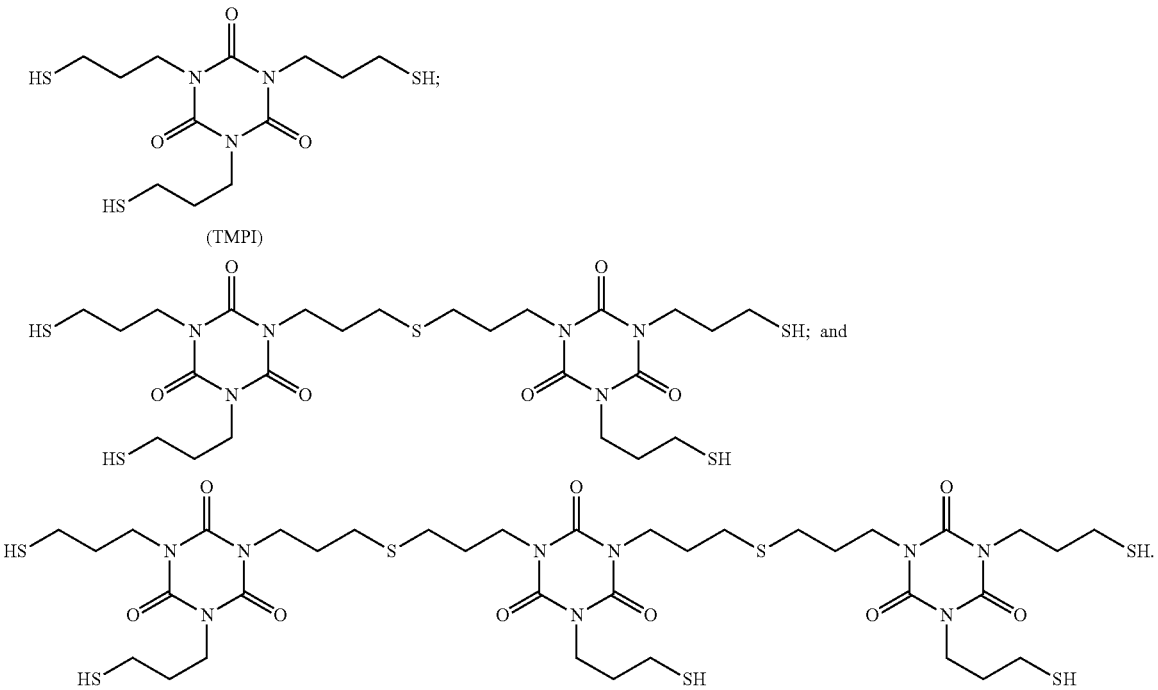

TABLE III

| Polythiol Compositions of Examples 15-21. | | | | | | | |
|---|---|---|---|---|---|---|---|
| Example Number | 15 | 16 | 17 | 18 | 19 | 20 | 21 |
| Reactor | 5-L | 5-L | 5-L | 5-L | 5-L | 379-L | Ex. 20 After WFE |
| Weight TAIC (g) | 240 | 240 | 240 | 147 | 350 | $1.73 \times 10^4$ | |
| Weight H$_2$S (g) | 3000 | 3000 | 3000 | 3000 | 2900 | $2.13 \times 10^5$ | |
| Weight TEP (g) | 0.24 | 1.2 | 1.2 | 0 | 0.35 | $5.22 \times 10^2$ | |
| Weight Irg 500 (g) | 0.24 | 0.24 | 0.24 | 1.0 | 0.35 | $1.72 \times 10^2$ | |
| H$_2$S Molar Ratio | 30 | 30 | 30 | 50 | 20 | 30 | |
| Reaction Time (min) | 15 | 5 | 5 | 10 | 12 | 20 | |
| % Conversion | 91 | 100 | 100 | <5 | 100 | 100 | |
| Wt. % TEP | 0.10 | 0.50 | 0.50 | 0 | 0.10 | 3.0 | |
| Wt. % Irg 500 | 0.10 | 0.10 | 0.10 | 0.68 | 0.10 | 0.10 | |
| Moles TAIC | 0.96 | 0.96 | 0.96 | 0.59 | 1.40 | 0.15 | |
| Olefin equivalents | 2.89 | 2.89 | 2.89 | 1.77 | 4.21 | 0.46 | |
| Moles TEP | 0.00144 | 0.00722 | 0.00722 | 0 | 0.00211 | 0.00692 | |
| Moles Irg 500 | 0.00129 | 0.00129 | 0.00129 | 0.00538 | 0.00188 | 0.00204 | |
| Mole % TEP | 0.050 | 0.250 | 0.250 | 0 | 0.050 | 1.506 | |
| Mole % Irg 500 | 0.045 | 0.045 | 0.045 | 0.304 | 0.045 | 0.444 | |
| Wt. % SH | 24.09 | 25.81 | — | 25.04 | 25.33 | 24.60 | 25.14 |
| Wt. % Total S | 24.81 | 26.21 | 25.87 | 26.78 | 26.48 | 24.70 | 25.89 |
| % mono-S | — | 0 | 0.15 | — | 0.1 | — | 0.0 |
| % DiS | — | 4.10 | 5.30 | — | 4.20 | — | 3.50 |
| % TMPI | — | 95.15 | 90.60 | — | 94.50 | — | 93.75 |
| % Heavies | — | 0.75 | 3.95 | — | 1.20 | — | 2.75 |

TABLE IV

Polythiol Compositions of Examples 22-29.

| Example Number | 22 | 23 | 24 | 25 | 26 | 27 | 28 | 29 |
|---|---|---|---|---|---|---|---|---|
| Reactor | 5-L | 5-L | 5-L | 5-L | 5-L | 5-L | 5-L | 5-L |
| Weight TAIC (g) | 147 | 236 | 236 | 236 | 236 | 236 | 236 | 337 |
| Weight $H_2S$ (g) | 3000 | 3000 | 3000 | 3000 | 3000 | 3000 | 3000 | 3000 |
| Weight TEP (g) | 8 | 1.0 | 0.5 | 0.25 | 0.25 | 0.25 | 0.25 | 0.35 |
| Weight Irg 500 (g) | 0.3 | 1.0 | 0.5 | 0.25 | 0.25 | 0 | 0.25 | 0.35 |
| $H_2S$ Molar Ratio | 50 | 30 | 30 | 30 | 30 | 30 | 30 | 22 |
| Reaction Time (min) | 15 | 7 | 10 | 10 | 10 | 15 | 10 | 12 |
| % Conversion | >99 | 99 | 99 | 99 | 99 | 98 | 97 | >98 |
| Wt. % SH | 24.3 | 25.2 | 25.6 | 26.6 | 27.3 | 25.5 | 25.4 | 25.6 |
| Wt. % Total S | 26.1 | 26.0 | 26.6 | 25.8 | 26.9 | 25.1 | 26.3 | 24.4 |
| SHEW (g/eq) | 131.9 | 127.2 | 125.2 | 120.5 | 117.4 | 125.7 | 126.2 | 125.2 |

The invention has been described above with reference to numerous embodiments and specific examples. Many variations will suggest themselves to those skilled in the art in light of the above detailed description. All such obvious variations are within the full intended scope of the appended claims. Other embodiments of the invention can include, but are not limited to, the following:

Embodiment A

A polythiol composition comprising polythiol molecules having the structures:

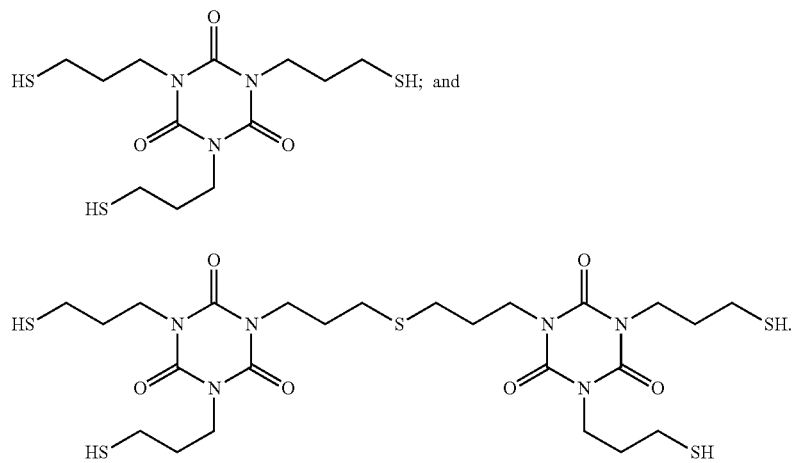

Embodiment B

The composition of embodiment A, further comprising a polythiol molecule having the structure:

Embodiment C

The composition of embodiment A or B, wherein polythiol molecules having at least three SH groups have an average thiol sulfur to sulfide sulfur molar ratio in any range of average thiol sulfur to sulfide sulfur molar ratios disclosed herein, e.g., from 2:1 to 1000:1, from 2:1 to 100:1, from 3:1 to 50:1, etc.

Embodiment D

The composition of any one of embodiments A to C, wherein polythiol molecules having at least three SH groups have an average mole percentage of sulfide sulfur in any range of average mole percentages of sulfide sulfur disclosed herein, e.g., from 0.1 to 33 mole %, from 1 to 30 mole %, from 2 to 20 mole %, etc.

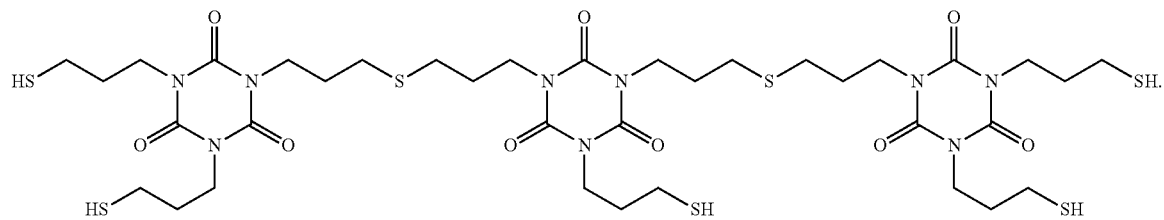 [SMILES: O=c1n(CCCS)c(=O)n(CCCSCCCn2c(=O)n(CCCS)c(=O)n(CCCSCCCn3c(=O)n(CCCS)c(=O)n(CCCS)c3=O)c2=O)c(=O)n1CCCS]

Embodiment E

The composition of any one of embodiments A to D, wherein polythiol molecules having at least three SH groups have an average mole percentage of thiol sulfur in any range of average mole percentages of thiol sulfur disclosed herein, e.g., from 67 to 99 mole %, from 68 to 98 mole %, from 75 to 98 mole %, etc.

Embodiment F

The composition of any one of embodiments A to E, wherein polythiol molecules having at least three SH groups have a SHEW in any range of SHEW's disclosed herein, e.g., from 118 to 190 g/eq, from 120 to 140 g/eq, from 120 to 130 g/eq, etc.

Embodiment G

The composition of any one of embodiments A to F, wherein the composition is produced by a process comprising:
1) contacting an unsaturated compound having the structure:

a)
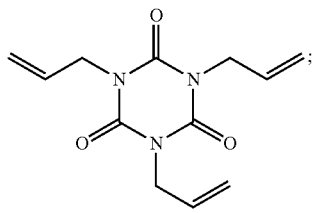

b) H$_2$S; and
c) a phosphite compound; and
2) forming the polythiol composition;
wherein a molar ratio of H$_2$S to carbon-carbon double bonds of the unsaturated compound is in a range from 5:1 to 500:1.

Embodiment H

The composition of embodiment G, wherein the process further comprises a step of removing at least a portion of the H$_2$S, of the phosphite compound, of the unsaturated compound, of compounds having two or less sulfur atoms, or combinations thereof, from the polythiol composition.

Embodiment I

The composition of embodiment H, wherein the H$_2$S, the phosphite compound, the unsaturated compound, the compounds having two or less sulfur atoms, or combinations thereof, are removed by wiped film evaporation, distillation, short path distillation, or a combination thereof.

Embodiment J

A polythiol composition comprising polythiol molecules having the structures:

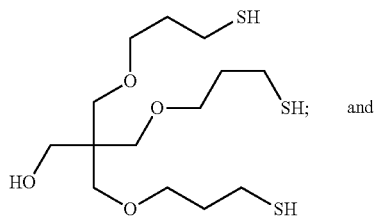

Embodiment K

The composition of embodiment J, further comprising:

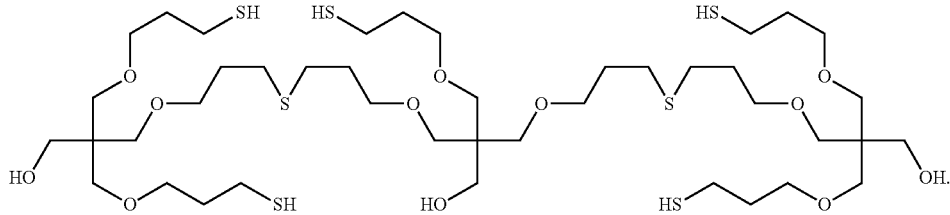 [SMILES: OCC(COCCCS)(COCCCS)COCCCSCCCOCC(CO)(COCCCS)COCCCSCCCOCC(CO)(COCCCS)COCCCS]

Embodiment L

The composition of embodiment J or K, wherein polythiol molecules having at least three SH groups have an average thiol sulfur to sulfide sulfur molar ratio in any range of average thiol sulfur to sulfide sulfur molar ratios disclosed herein, e.g., from 2:1 to 1000:1, from 2:1 to 100:1, from 3:1 to 50:1, etc.

Embodiment M

The composition of any one of embodiments J to L, wherein polythiol molecules having at least three SH groups have an average mole percentage of sulfide sulfur in any range of average mole percentages of sulfide sulfur disclosed herein, e.g., from 0.1 to 33 mole %, from 1 to 30 mole %, from 2 to 20 mole %, etc.

Embodiment N

The composition of any one of embodiments J to M, wherein polythiol molecules having at least three SH groups have an average mole percentage of thiol sulfur in any range of average mole percentages of thiol sulfur disclosed herein, e.g., from 67 to 99 mole %, from 68 to 98 mole %, from 75 to 98 mole %, etc.

Embodiment O

The composition of any one of embodiments J to N, wherein polythiol molecules having at least three SH groups have a SHEW in any range of SHEW's disclosed herein, e.g., from 120 to 190 g/eq, from 122 to 140 g/eq, from 122 to 130 g/eq, etc.

Embodiment P

The composition of any one of embodiments J to O, wherein the composition is produced by a process comprising:
1) contacting an unsaturated compound having the structure:
a)

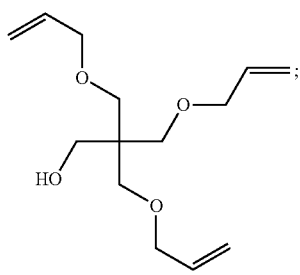

b) $H_2S$; and
c) a phosphite compound; and
2) forming the polythiol composition;
wherein a molar ratio of $H_2S$ to carbon-carbon double bonds of the unsaturated compound is in a range from 5:1 to 500:1.

Embodiment Q

The composition of embodiment P, wherein the process further comprises a step of removing at least a portion of the $H_2S$, of the phosphite compound, of the unsaturated compound, of compounds having two or less sulfur atoms, or combinations thereof, from the polythiol composition.

Embodiment R

The composition of embodiment Q, wherein the $H_2S$, the phosphite compound, the unsaturated compound, the compounds having two or less sulfur atoms, or combinations thereof, are removed by wiped film evaporation, distillation, short path distillation, or a combination thereof.

Embodiment S

A polythiol composition comprising polythiol molecules having the formulas:

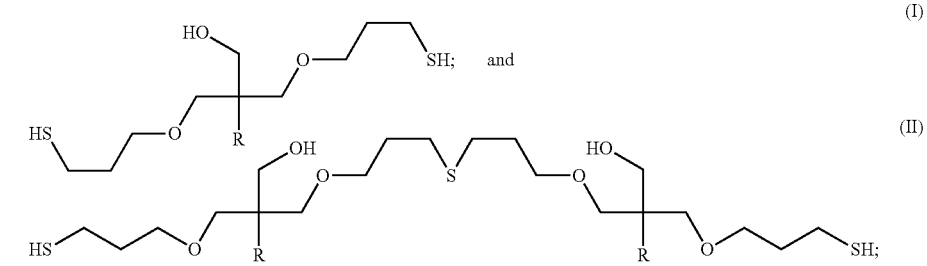

wherein R is any $C_1$-$C_{18}$ hydrocarbyl group disclosed herein.

Embodiment T

The composition of embodiment S, further comprising polythiol molecules having the formula:

(III)

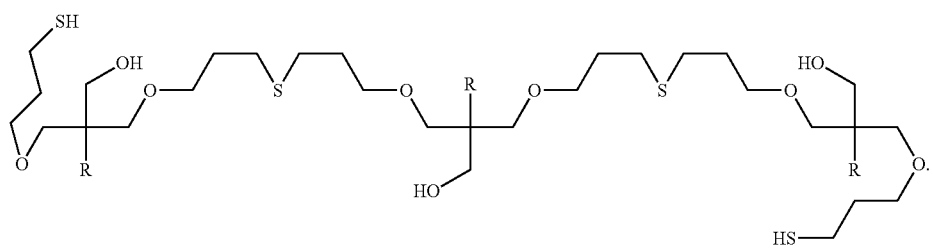

Embodiment U

The composition of embodiment S or T, wherein polythiol molecules having at least two SH groups have an average thiol sulfur to sulfide sulfur molar ratio in any range of average thiol sulfur to sulfide sulfur molar ratios disclosed herein, e.g., from 1:1.5 to 1000:1, from 1:1 to 100:1, from 2:1 to 50:1, etc.

Embodiment V

The composition of any one of embodiments S to U, wherein polythiol molecules having at least two SH groups have an average mole percentage of sulfide sulfur in any range of average mole percentages of sulfide sulfur disclosed herein, e.g., from 0.1 to 60 mole %, from 1 to 55 mole %, from 5 to 30 mole %, etc.

Embodiment W

The composition of any one of embodiments S to V, wherein polythiol molecules having at least two SH groups have an average mole percentage of thiol sulfur in any range of average mole percentages of thiol sulfur disclosed herein, e.g., from 40 to 99 mole %, from 50 to 97 mole %, from 70 to 97 mole %, etc.

Embodiment X

The composition of any one of embodiments S to W, wherein polythiol molecules having at least two SH groups have a SHEW in any range of SHEW's disclosed herein, e.g., from 142 to 350 g/eq, from 144 to 175 g/eq, from 145 to 165 g/eq, etc.

Embodiment Y

The composition of any one of embodiments S to X, wherein the composition is produced by a process comprising:
1) contacting an unsaturated compound having the formula a)

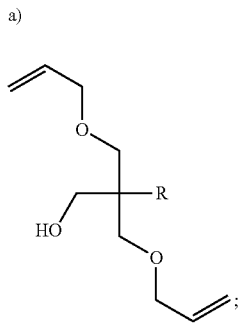

(IV)

b) $H_2S$; and
c) a phosphite compound; and
2) forming the polythiol composition;
wherein a molar ratio of $H_2S$ to carbon-carbon double bonds of the unsaturated compound is in a range from 5:1 to 500:1.

Embodiment Z

The composition of embodiment Y, wherein the process further comprises a step of removing at least a portion of the $H_2S$, of the phosphite compound, of the unsaturated compound, of compounds having only one sulfur atom, or combinations thereof, from the polythiol composition.

Embodiment AA

The composition of embodiment Z, wherein the $H_2S$, the phosphite compound, the unsaturated compound, the compounds having only one sulfur atom, or combinations thereof, are removed by wiped film evaporation, distillation, short path distillation, or a combination thereof.

Embodiment BB

The composition of any one of embodiments S to AA, wherein R is a $C_1$-$C_{10}$ alkyl group.

Embodiment CC

The composition of any one of embodiments S to BB, wherein R is an ethyl group.

Embodiment DD

The composition of any one of embodiments G to I, P to R, or Y to AA, wherein the molar ratio of $H_2S$ to carbon-carbon double bonds of the unsaturated compound is in any range of molar ratios of $H_2S$ to carbon-carbon double bonds disclosed herein, e.g., from 15:1 to 150:1, from 20:1 to 75:1; from 20:1 to 50:1, etc.

Embodiment EE

The composition of embodiment DD, wherein a molar ratio of the phosphite compound to carbon-carbon double bonds of the unsaturated compound is in any range of molar ratios of the phosphite compound to carbon-carbon double bonds disclosed herein, e.g., from 0.0005:1 to 0.10:1, from 0.006:1 to 0.05:1, etc.

Embodiment FF

The composition of embodiment DD or EE, wherein the phosphite compound comprises a compound having the formula, $P(OR^1)_3$, wherein each $R^1$ is independently any $C_1$-$C_{10}$ hydrocarbyl group disclosed herein.

Embodiment GG

The composition of any one of embodiments DD to FF, wherein the phosphite compound comprises trimethylphosphite, triethylphosphite, tributylphosphite, or any combination thereof.

Embodiment HH

The composition of any one of embodiments DD to GG, wherein the polythiol composition is formed at a temperature in any range of temperatures disclosed herein, e.g., from −30° C. to 80° C., from 0° C. to 45° C., etc.

Embodiment II

The composition of any one of embodiments DD to HH, wherein the polythiol composition is formed in the presence of electromagnetic radiation.

Embodiment JJ

The composition of any one of embodiments DD to II, wherein the polythiol composition is formed in the presence of ultraviolet light.

Embodiment KK

The composition of any one of embodiments DD to JJ, wherein the polythiol composition is formed in the presence of ultraviolet light and a photoinitiator, and wherein the photoinitiator is present at an amount within any weight percentage range disclosed herein, e.g., from 0.05 to 5 wt. %, from 0.5 to 3 wt. %, etc., based on the weight of the unsaturated compound.

Embodiment LL

The composition of any one of embodiments DD to HH, wherein the polythiol composition is formed in the presence of a free radical initiator, and wherein the free radical initiator is present at an amount within any weight percentage range disclosed herein, e.g., from 0.1 to 9 wt. %, from 0.1 to 2 wt. %, etc., based on the weight of the unsaturated compound.

Embodiment MM

The composition of embodiment LL, wherein the polythiol composition is formed at conditions suitable for a thermal decomposition of the free radical initiator.

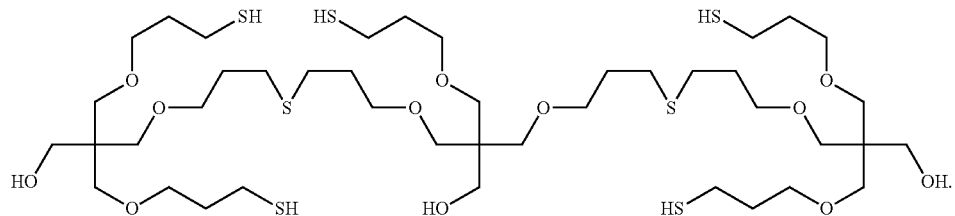 [SMILES: OCC(COCCCS)(COCCCS)COCCCSCCCOCC(CO)(COCCCS)COCCCSCCCOCC(CO)(COCCCS)COCCCS]

Embodiment NN

The composition of any one of embodiments DD to MM, wherein the polythiol composition is formed in the presence of any solvent disclosed herein, e.g., a hydrocarbon solvent, an aromatic hydrocarbon solvent, a ketone solvent, an alcohol solvent, an ether solvent, or any combination thereof.

Embodiment OO

The composition of any one of embodiments DD to NN, wherein at least 90% of the carbon-carbon double bonds of the unsaturated compound have reacted to form a sulfur-containing group.

Embodiment PP

An article of manufacture comprising the composition of any one of embodiments A to OO.

Embodiment QQ

An article of manufacture comprising the composition of any one of embodiments A to OO, wherein the article is a coating, a paint, or an adhesive.

We claim:

1. A polythiol composition comprising polythiol molecules having the structures:

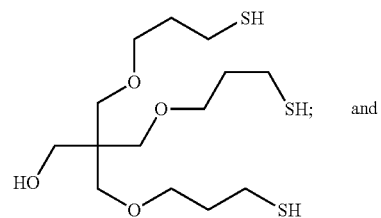

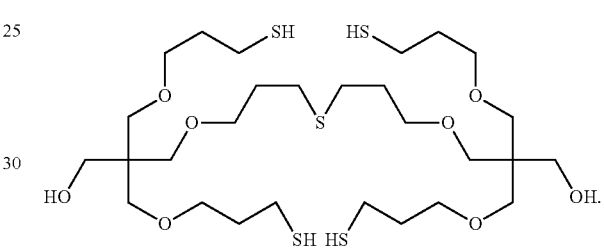

2. The composition of claim 1, further comprising:

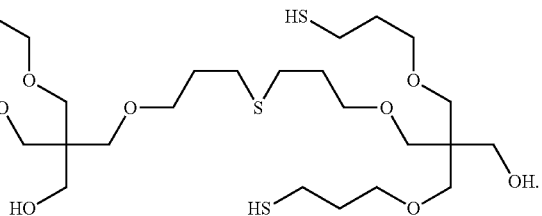

3. The composition of claim 1, wherein polythiol molecules having at least three SH groups have:
   an average thiol sulfur to sulfide sulfur molar ratio in a range from 2:1 to 1000:1;
   an average of from 0.1 mole % to 33 mole % sulfide sulfur, based on the total sulfur of polythiol molecules having at least three SH groups;
   an average of from 67 mole % to 99 mole % thiol sulfur, based on the total sulfur of polythiol molecules having at least three SH groups;
   a mercaptan equivalent weight in a range from 120 to 190 g/eq; or
   any combination thereof.

4. The composition of claim 1, wherein polythiol molecules having at least three SH groups have:
   an average thiol sulfur to sulfide sulfur molar ratio in a range from 3:1 to 50:1;
   an average of from 2 mole % to 20 mole % sulfide sulfur, based on the total sulfur of polythiol molecules having at least three SH groups;

an average of from 75 mole % to 98 mole % thiol sulfur, based on the total sulfur of polythiol molecules having at least three SH groups;

a mercaptan equivalent weight in a range from 122 to 140 g/eq; or any combination thereof.

5. An adhesive comprising the polythiol composition of claim 1.

6. The composition of claim 1, wherein the composition is produced by a process comprising:
1) contacting:
   a) pentaerythritol triallyl ether;
   b) $H_2S$; and
   c) a phosphite compound; and
2) forming the polythiol composition;
wherein a molar ratio of $H_2S$ to carbon-carbon double bonds of pentaerythritol triallyl ether is in a range from 5:1 to 500:1.

7. The composition of claim 6, wherein the phosphite compound comprises a compound having the formula:

$P(OR^1)_3$;

wherein each $R^1$ is independently a $C_1$-$C_{10}$ hydrocarbyl group.

8. The composition of claim 6, wherein:
the molar ratio of $H_2S$ to carbon-carbon double bonds of pentaerythritol triallyl ether is in a range from 5:1 to 100:1; and
a molar ratio of the phosphite compound to carbon-carbon double bonds of pentaerythritol triallyl ether is in a range from 0.0005:1 to 0.10:1.

9. The composition of claim 6, wherein the polythiol composition is formed in the presence of ultraviolet light.

10. The composition of claim 6, wherein the polythiol composition is formed in the presence of ultraviolet light and a photoinitiator, wherein the photoinitiator is present at an amount in a range from 0.05 to 5 wt. %, based on the weight of pentaerythritol triallyl ether.

11. The composition of claim 6, wherein the polythiol composition is formed in the presence of a hydrocarbon solvent, an aromatic hydrocarbon solvent, a ketone solvent, an alcohol solvent, an ether solvent, or any combination thereof.

12. The composition of claim 6, wherein the process further comprises a step of removing at least a portion of the $H_2S$, of the phosphite compound, of pentaerythritol triallyl ether, of compounds having two or less sulfur atoms, or combinations thereof, from the polythiol composition.

13. An article of manufacture comprising the polythiol composition of claim 1.

14. A coating or paint composition comprising an additive and the polythiol composition of claim 1.

15. The composition of claim 1, wherein polythiol molecules having at least three SH groups have an average thiol sulfur to sulfide sulfur molar ratio in a range from 2:1 to 1000:1.

16. The composition of claim 1, wherein polythiol molecules having at least three SH groups have an average thiol sulfur to sulfide sulfur molar ratio in a range from 3:1 to 50:1.

17. The composition of claim 1, wherein polythiol molecules having at least three SH groups have an average of from 0.1 mole % to 33 mole % sulfide sulfur, based on the total sulfur of polythiol molecules having at least three SH groups.

18. The composition of claim 1, wherein polythiol molecules having at least three SH groups have an average of from 2 mole % to 20 mole % sulfide sulfur, based on the total sulfur of polythiol molecules having at least three SH groups.

19. The composition of claim 1, wherein polythiol molecules having at least three SH groups have an average of from 67 mole % to 99 mole % thiol sulfur, based on the total sulfur of polythiol molecules having at least three SH groups.

20. The composition of claim 1, wherein polythiol molecules having at least three SH groups have an average of from 75 mole % to 98 mole % thiol sulfur, based on the total sulfur of polythiol molecules having at least three SH groups.

21. The composition of claim 1, wherein polythiol molecules having at least three SH groups have a mercaptan equivalent weight in a range from 120 to 190 g/eq.

22. The composition of claim 1, wherein polythiol molecules having at least three SH groups have a mercaptan equivalent weight in a range from 122 to 140 g/eq.

* * * * *